(12) United States Patent
Guerrini

(10) Patent No.: US 10,525,199 B2
(45) Date of Patent: Jan. 7, 2020

(54) METHOD AND CONTROL DEVICE FOR CONTROLLING THE ADMINISTRATION OF INSULIN TO A PATIENT

(71) Applicant: Fresenius Vial SAS, Brézins (FR)

(72) Inventor: Alexandre Guerrini, Voiron (FR)

(73) Assignee: Fresenius Vial SAS, Brézins (FR)

( * ) Notice: Subject to any disclaimer, the term of this patent is extended or adjusted under 35 U.S.C. 154(b) by 65 days.

(21) Appl. No.: 14/890,665

(22) PCT Filed: Jan. 31, 2014

(86) PCT No.: PCT/EP2014/051927
§ 371 (c)(1),
(2) Date: Nov. 12, 2015

(87) PCT Pub. No.: WO2014/202233
PCT Pub. Date: Dec. 24, 2014

(65) Prior Publication Data
US 2016/0089494 A1    Mar. 31, 2016

(30) Foreign Application Priority Data

Jun. 21, 2013  (EP) .................................... 13305853

(51) Int. Cl.
*A61M 5/172*    (2006.01)
*G06F 19/00*    (2018.01)

(52) U.S. Cl.
CPC ....... *A61M 5/1723* (2013.01); *G06F 19/3468* (2013.01); *A61M 2205/33* (2013.01); *A61M 2205/50* (2013.01)

(58) Field of Classification Search
CPC ........ A61M 5/1723; A61M 2205/3334; A61M 2205/3331; A61M 2205/3327;
(Continued)

(56) References Cited

U.S. PATENT DOCUMENTS 6,510,353 B1 *   1/2003   Gudaz ................ G05B 19/0428
                                                          700/37
7,060,059 B2 *   6/2006   Keith ..................... A61K 38/28
                                                          604/504
(Continued)

FOREIGN PATENT DOCUMENTS

JP    2010-512945 A    4/2010
WO    WO 2008/030347    3/2008
WO    WO 2011/089600    7/2011

OTHER PUBLICATIONS

Chee et al; "Closed-loop glucose control in critically ill patients using continuous glucose monitoring system (CGMS) in real time"; IEEE Transactions on Information Technology in Biomedicine ( vol. 7 , Issue: 1 , Mar. 2003) (Year: 2003).*

(Continued)

*Primary Examiner* — Nathan R Price
*Assistant Examiner* — Tasnim Mehjabin Ahmed
(74) *Attorney, Agent, or Firm* — Cook Alex Ltd.

(57) ABSTRACT

In a method for controlling the administration of insulin to a patient, a target glucose level is set and a controller computes a recommended infusion rate based on the target glucose level and a measured glucose level of a patient for administering insulin to the patient. The controller uses a controller gain for computing the recommended infusion rate. Herein, an insulin sensitivity of the patient is determined using a mathematical model taking into account the measured glucose level and an actual infusion rate of insulin administered to the patient and, based on the insulin sensitivity, the controller gain of the controller is determined. In this way a method for controlling the administration of insulin to a patient is provided which in a reliable, compu- (Continued)

tationally efficient manner allows for maintaining a patient's blood glucose level at or around a desired target glucose level.

16 Claims, 14 Drawing Sheets

(58) Field of Classification Search
CPC .......... A61M 2205/50; A61M 2205/52; A61M 2205/3507; A61M 2005/14208; A61M 2230/203; G06F 19/3456; A61B 5/14532; A61B 5/4836; A61B 5/4839
See application file for complete search history.

(56) References Cited

U.S. PATENT DOCUMENTS

| | | | |
|---|---|---|---|
| 2003/0130616 A1* | 7/2003 | Steil | A61B 5/14532 604/66 |
| 2004/0220517 A1* | 11/2004 | Starkweather | A61M 5/172 604/67 |
| 2007/0173761 A1 | 7/2007 | Kanderian, Jr. et al. | |
| 2008/0183060 A1* | 7/2008 | Steil | A61B 5/14532 600/365 |
| 2011/0077493 A1 | 3/2011 | Shadforth et al. | |

OTHER PUBLICATIONS

International Search Report, counterpart International Appl. No. PCT/EP2014/051927 (dated Sep. 29, 2014) (3 pages).
Written Opinion of the International Preliminary Examining Authority, counterpart International Appl. No. PCT/EP2014/051927 (dated May 22, 2015) (9 pages).
Hann et al., Integral-based parameter identification for long-term dynamic verification of a glucose-insulin system model, *Computer Methods and Programs in Biomedicine*, vol. 77, No. 3, pp. 259-270 (Mar. 1, 2005) (Elsevier, NL).
Holterhus et al., Classification of distinct baseline insulin infusion patterns in children and adolescents with type 1 diabetes on continuous subcutaneous insulin therapy, *Diabetes Care*, vol. 30, No. 3, pp. 568-573 (Mar. 1, 2007) (US).
Ariyur, K. et al., Real-Time Optimization by Extremum-Seeking Control, Ch. 4, pp. 61-70 (2003).
Bergman, R. et al., *Physiologic Evaluation of Factors Controlling Glucose Tolerance in Man*, J. Clinical Investigation, Vol, 68, pp. 1456-1467 (Dec. 1981).
Choi, J. et al., *Extremum Seeking Control for Discrete Time Systems*, IEEE Trans Automatic Control, vol. 47, No. 2, pp. 318-323 (Feb. 2002).
Doran, C., *Modelling and Control of Hyperglycemia in Critical Care Patients*, Thesis, University of Canterbury, Christchurch, New Zealand (Mar. 2004).
Finfer, S. et al., *Intensive versus Conventional Glucose Control in Critically Ill Patients*, New Eng. J. Med., vol. 360, No. 13, pp. 1283-1297 (Mar. 26, 2009).
Finfer, S. et al., Nice-Sugar Study Statistical Analysis Plan (circa 2008).
Ha N, C. et al., *Integral-based parameter identification for long-term dynamic verification of a glucose-insulin system model*, Computer Methods and Programs in Biomedicine, pp. 259-270 (2005).
Herpe, T. et al., *Glycemia Prediction in Critically Ill Patients Using an Adaptive Modeling Approach*, J. Diabetes Sci. Tech., vol. 1, Issue 3, pp. 348-356 (May 2007).
Keener, J. et al., Mathematical Physiology, Systems Physiology, pp. 803-806 (2d ed. 2009).
Killingsworth, N. et al., *Auto-Tuning of PID Controllers via Extremum Seeking*, American Control Conf., pp. 2251-2256 (Jun. 2005).
Kovacs, L. et al., *Nonlinear Control Analysis of an ICU Model for Tight Glycaemic Control*, Proc. 18$^{th}$ World Cong., Int'l Fed'n Automatic Control, pp. 1739-1744 (Aug./Sep. 2011).
Krstic, M., *Performance improvement and limitations in extremum seeking control*, Sys. & Control Letters, vol. 39, pp. 313-326 (2000).
Krstic, M. et al., *Stability of extremum seeking feedback for general nonlinear dynamic systems*, Automatica, 36, pp. 595-601 (2000).
Mackenzie, I. et al., *The metrics of glycaemic control in critical care*, Intensive Care Med., vol. 37, pp. 435-443 (2011).
Nice (Sugar) Study Protocol (circa 2008).
Nice Sugar Study Treatment Algorithm (circa 2008).
Prigeon, R. et al., *The Effect of Insulin Dose on the Measurement of Insulin Sensitivity by the Minimal Model Technique*, J. Clinical Investigation, vol. 97, No. 2, pp. 501-507 (Jan. 1996).
Rizza, R. et al., *Dose-response characteristics for effects of insulin on production and utilization of glucose in man*, Am. Physiological Soc'y, pp. E630-E639 (1981).

\* cited by examiner

METHOD AND CONTROL DEVICE FOR CONTROLLING THE ADMINISTRATION OF INSULIN TO A PATIENT

The present application is a U.S. National Stage of PCT International Patent Application No. PCT/EP2014/051927, filed Jan. 31, 2014, which claims priority to EP Application No. 13305853.7, filed Jun. 21, 2013, both of which are hereby incorporated herein by reference.

Description

The invention relates to a method for controlling the administration of insulin to a patient according to the preamble of claim 1 and to a control device for controlling the administration of insulin to a patient.

With a method of this kind a target glucose level is set which shall be, at least approximately, reached within a patient. A controller then computes a recommended infusion rate based on the target glucose level and further based on a measured glucose level of the patient for administering insulin to the patient. The controller herein comprises a controller gain for computing the recommended infusion rate such that, based on the target glucose level and the measured glucose level as input variables and using the controller gain as control parameter, the recommended infusion rate for administering insulin to the patient may be determined.

A method of this kind and a corresponding control device for carrying out such a method may in particular be used to control the blood glucose level of critically ill patients. For such critically ill patients, which for example are treated in an intensive care unit (ICU) of a hospital, an increase of the blood glucose level may occur in situations of stress, leading to hyperglycaemia. This phenomenon, usually called "stress-induced diabetes", has been shown to potentially be responsible for complications during a patient treatment, leading to for example an increased length of stay of the patient in a hospital or even death.

To counteract such unwanted effects of stress-induced diabetes it nowadays is common to infuse insulin to a critically ill patient on a continuous basis in order to lower the blood glucose level to a specific, predefined level (so called normoglycaemia, corresponding to a blood glucose level of about 4.4 to 6.1 mmol/L). However, the desired target range for the blood glucose level is still a topic of discussion, and there exist few clinically tested, functional protocols to ensure a reliable controlling of the blood glucose level to be within an acceptable range.

From WO 2008/030347 A2 a method for making intelligent therapy recommendations for insulin pump parameters is known. The pump parameters include basal rates, carbohydrate-to-insulin ratios, and insulin sensitivity factors. A determination of whether a therapy recommendation should be made is based on comparing an updated recommended change with a threshold. The updated recommended change to the pump parameter is made based on a previous recommended change to the pump parameter and the difference between a current blood glucose value and a targeted blood glucose level.

In a method disclosed by WO 2011/089600 A1, an insulin dose is recommended in that blood glucose data is received, one or more insulin sensitivity values are determined associated with the blood glucose data and an insulin dose is determined based on the one or more insulin sensitivity values. The insulin sensitivity values herein may for example be determined by selecting one or more insulin sensitivity values from a table, calculating the one or more insulin sensitivity values or modelling or correlating the one or more insulin sensitivity values with respect to empirical data.

In a publication by Christopher E. Hann et al., "Integral-based parameter identification for long-term dynamic verification of a glucose-insulin system model", Computer Methods and Programs in Biomedicine (2005) 77, 259-270, a model using time-varying patient specific parameters for glucose effectiveness and insulin sensitivity in a patient is described.

There is a desire for a safe method for controlling the administration of insulin to a patient which allow in a fast, reliable manner to maintain a patient's blood glucose level at or around a desired target value, in particular to reduce the risk for hyperglycaemia in critically ill patients.

It is an object of the instant invention to provide a method and a control device for controlling the administration of insulin to a patient which in a reliable, computationally efficient manner allow for maintaining a patient's blood glucose level at or around a desired target glucose level.

This object is achieved with a method comprising the features of claim 1.

Accordingly, an insulin sensitivity of the patient is determined by means of a mathematical model taking into account the measured glucose level and an actual infusion rate of insulin administered to the patient and based on the insulin sensitivity the controller gain of the controller is determined.

Advantageously, the controller, when computing the recommended infusion rate based on the target glucose level and the measured glucose level, in addition takes also a glucose intake value of the patient into account. The glucose intake of the patient herein may be taken into account directly as a parameter when computing the recommended infusion rate. Or the glucose intake may be taken into account indirectly via the mathematical model when determining the insulin sensitivity. The insulin sensitivity hence is determined using a mathematical model taking into account, as parameters, the measured glucose level, the actual infusion rate and the glucose intake by the patient.

The instant invention is based on the idea to use a mathematical model to determine a value for the specific, situation-dependent insulin sensitivity of a patient. The model takes into account the actually measured glucose level within a patient and an actual infusion rate of insulin administered to the patient. Further, for example a glucose intake (for example due to nutrients fed to a patient) is taken into account. The model sets the actual infusion rate and the blood glucose level into relation with each other, wherein the relation is, among others, defined by the insulin sensitivity and in addition for example by a glucose clearance rate. By adapting the insulin sensitivity and/or the glucose clearance rate the actual infusion rate may be matched to the measured glucose level such that the model predicts an accurate glucose level upon administration of insulin to the patient at the particular infusion rate. The insulin sensitivity determined in this way is then used to set the controller gain of the controller, such that by means of the controller gain and by taking into account the actually measured glucose level an updated infusion rate may be determined.

In particular, the model may be used to determine the insulin sensitivity of the patient anew for each measured glucose level. Hence, for each blood glucose level measurement a new insulin sensitivity value is determined, which hence reflects changing conditions of a patient and hence is situation-dependent. Based on the newly determined insulin sensitivity value, then, the controller gain is modified, and the controller computes an updated recommended infusion rate based on the currently measured glucose level and the target glucose level using the modified controller gain.

The controller, in one embodiment, also computes a proposed time for next measurement for measuring a glucose level of a patient. A nurse hence does not only obtain, as output from the method, a recommended infusion rate for administering insulin to a patient, but also a recommended time for next measurement. The time-for-next-recommendation module uses for example the current and last blood glucose level measurements along with the glucose intakes to determine the recommended time, but, in one embodiment, does not directly depend on the insulin sensitivity classes.

The model preferably is a so called pharmacokinetic-pharmacodynamic (PkPd) model taking into account patient-specific parameters such as the patient's height, weight, age, gender, body mass index (BMI), ideal BMI, relative ideal BMI and/or diabetes status to model the pharmacodynamics and pharmacokinetics of the glucose-insulin system of the patient.

Such model is for example known from the publication of Christopher E. Hann et al., "Integral-based parameter identification for long-termed dynamic verification of a glucose-insulin system model", Computer Methods and Programs in Biomedicine (2005) 77, 259-270, which shall be incorporated by reference herein.

The controller gain is set based on the insulin sensitivity value which has been determined using the model. The controller gain herein may be set by associating the insulin sensitivity value provided by the model to a predefined insulin sensitivity class. Each insulin sensitivity class herein comprises a predefined controller gain such that, by associating the insulin sensitivity to a particular insulin sensitivity class, the controller gain is set to equal the controller gain associated with the particular insulin sensitivity class.

This is based on the idea to, in an advance step prior to actually administering insulin to a patient, determine a number of different, discrete insulin sensitivity classes. With each insulin sensitivity class herein a particular controller gain is associated. By then, during the actual administration procedure, assessing in what insulin sensitivity class the currently determined insulin sensitivity of the patient falls, it can in an easy and reliable manner be determined what controller gain is associated with that insulin sensitivity, namely the controller gain of the insulin sensitivity class the current insulin sensitivity value of the patient falls into.

By using such predefined insulin sensitivity classes, the determination of the controller gain based on a current insulin sensitivity of a patient becomes easy and computationally efficient. Namely, no intensive computations are necessary to compute the controller gain using a mathematical relation linking the insulin sensitivity directly to the controller gain. Rather, it simply can be checked into which insulin sensitivity class the actual insulin sensitivity falls such that the controller gain can then be set to the controller gain associated with that particular insulin sensitivity class.

If a patient's state changes during the stay in a hospital, also the insulin sensitivity may change such that it may fall into a different insulin sensitivity class. In that case, the controller gain is correspondingly modified to the controller gain of the newly determined, different insulin sensitivity class the insulin sensitivity value now falls into. The method hence may track changes in the patient's state and may switch the controller gain accordingly.

Additionally, there may be rules to prevent a cyclic controller gain switch if the patient's insulin sensitivity exhibits an oscillating behavior between two insulin sensitivity classes. In particular, if it is determined that for a time of measurement the insulin sensitivity is associated with a different insulin sensitivity class than for a previous time of measurement, the controller gain may be set according to the newly determined insulin sensitivity class if and only if a predefined additional switch criterion is satisfied.

For implementing this, several possible ways exist. For example, in one embodiment a "low-pass" rule may be used. For this it is assumed that a patient falls into a newly determined sensitivity class if and only if the determined insulin sensitivity of the patient corresponds to said sensitivity class for a specific predetermined period (e.g. a specific number of consecutive measurements, for example three measurements). Thus, if the patient's sensitivity class changes at a given time of measurement, but returns to the previous sensitivity class at the next measurement, there is no switch from one sensitivity class to another, i.e. for the purpose of setting the controller again the algorithm remains at the original sensitivity class. The controller considers the patient to be within the original sensitivity class for the entire period. The switch criterion hence in this case is that a newly determined insulin sensitivity class must remain valid for a predetermined minimum period, e.g. a predetermined number of consecutive measurements in order to switch to the new insulin sensitivity class for setting the controller gain.

In another embodiment, a hysteresis effect may be added, i.e. a threshold may be assumed which the determined insulin sensitivity must exceed in order to switch to a new sensitivity class. In this embodiment the switch criterion is whether a threshold is exceeded when changing from one sensitivity class to another.

The multiple insulin sensitivity classes are beneficially determined prior to administering insulin to a patient. Herein, each insulin sensitivity class may be defined by a stability parameter and a robustness parameter which are dependent on the insulin sensitivity that is determined by the model and the controller gain currently used by the controller. The insulin sensitivity classes hence are defined in a two-dimensional plane which is spanned by the stability parameter along one axis and by the robustness parameter along another axis.

The controller outputs the recommended infusion rate to an infusion pump. Herein, prior to infusing insulin to the patient using the recommended infusion rate the infusion pump may be required to request an approval by a nurse for administering insulin to the patient. Instead of approving, the nurse may modify the recommended infusion rate to use a different, modified infusion rate, which for example may be limited by an allowable range of infusion rates. Hence an interaction of a user, namely a nurse, is required prior to the actual administration of insulin to the patient, such that an semi-closed loop system (i.e. a system providing a feedback from a patient, but at the same time requiring an interaction by a nurse) is provided.

Alternatively, a closed-loop system may be provided in which the controller automatically outputs the recommended infusion rate to the pump, wherein the infusion pump uses the recommended infusion rate for a subsequent administration of insulin to a patient. If also a blood glucose level of the patient subsequently is measured automatically by means of an appropriate sensing device and if the measured blood glucose level is directly fed back to the controller and to the model, a closed-loop-system is provided which in an automatic fashion may allow for a controlled administration of insulin to a patient using adaptive infusion rates.

The controller, in one embodiment, is a so-called proportional-integral-derivative (PID) controller. Such PID controller uses a PID controller equation having a proportional term, an integral term and a derivative term which, in simple words, are indicative of a present error (proportional term), an accumulation of past errors (integral term) and a prediction of future errors (derivative term). The PID controller herein calculates an error value as the difference between a measured process variable, in the instant case a blood glucose level of a patient, and a desired setpoint, in this case the target glucose level. The controller, by means of optimizing its PID controller equation, attempts to minimize the error by adjusting the process control inputs.

The PID controller equation in addition may comprise a so-called compliance term for taking into account, when determining an updated recommended infusion rate, a deviation of the actual infusion rate from a previously determined recommended infusion rate. This is based on the idea to use an additional term in the conventional PID controller equation in order to take into account a modification to a recommended infusion rate that may have been done by a nurse operating the infusion pump. If a nurse does not confirm the recommended infusion rate provided by the controller, but rather modifies the infusion rate to use a different infusion rate, this by means of the compliance term can be taken into account when determining, based on a next blood glucose level measurement, an updated recommended infusion rate, which hence also reflects the modification previously entered by a nurse.

Within the method the controller gain is determined for use in the computation of the recommended infusion rate. In a PID controller each term (mainly the proportional term, the integral term and the derivative term) may be associated with a distinct gain, such that the controller gain may be constituted by a set of gains associated with the proportional term, the integral term and the derivative term of the PID controller equation. Hence, according to the insulin sensitivity provided by the model, not a single gain value but of a set of gain values is adjusted. For example, with each insulin sensitivity class a set of gains may be associated, such that an appropriate set of gains can in an easy, efficient manner be determined by assessing into which class a particular insulin sensitivity value falls.

The controller may furthermore use a saturation for determining the recommended infusion rate. This is based on the idea to include, into the PID controller equation, a saturation mechanism which ensures that the recommended infusion rate cannot rise above or fall below a range of acceptable infusion rates. If for example an infusion pump has a maximum infusion rate and a minimum infusion rate, by means of the saturation mechanism it shall be made sure that a recommended range falls into the range defined by such maximum and minimum rates. The saturation herein may be two-dimensional in that it also takes the measured blood glucose level into account for applying a saturation function depending on the blood glucose level.

The object is furthermore achieved by a control device for controlling the administration of insulin to a patient, the control device comprising:

a target setting unit for setting a target glucose level and
a controller for computing a recommended infusion rate based on the target glucose level and a measured glucose level of a patient for administering insulin to the patient, wherein the controller comprises a controller gain for computing the recommended infusion rate.

Herein, the device further comprises
a model unit for determining an insulin sensitivity of the patient by means of a mathematical model taking into account the measured glucose level and an actual infusion rate of insulin administered to the patient and
an adaption unit for determining, based on the insulin sensitivity, the controller gain of the controller.

The advantages and advantageous embodiments described above with regard to the method equally apply also to the control device, such that it shall be referred to the above.

The idea underlying the invention shall subsequently be described in more detail with regard to the embodiments shown in the figures. Herein:

Figure 1:
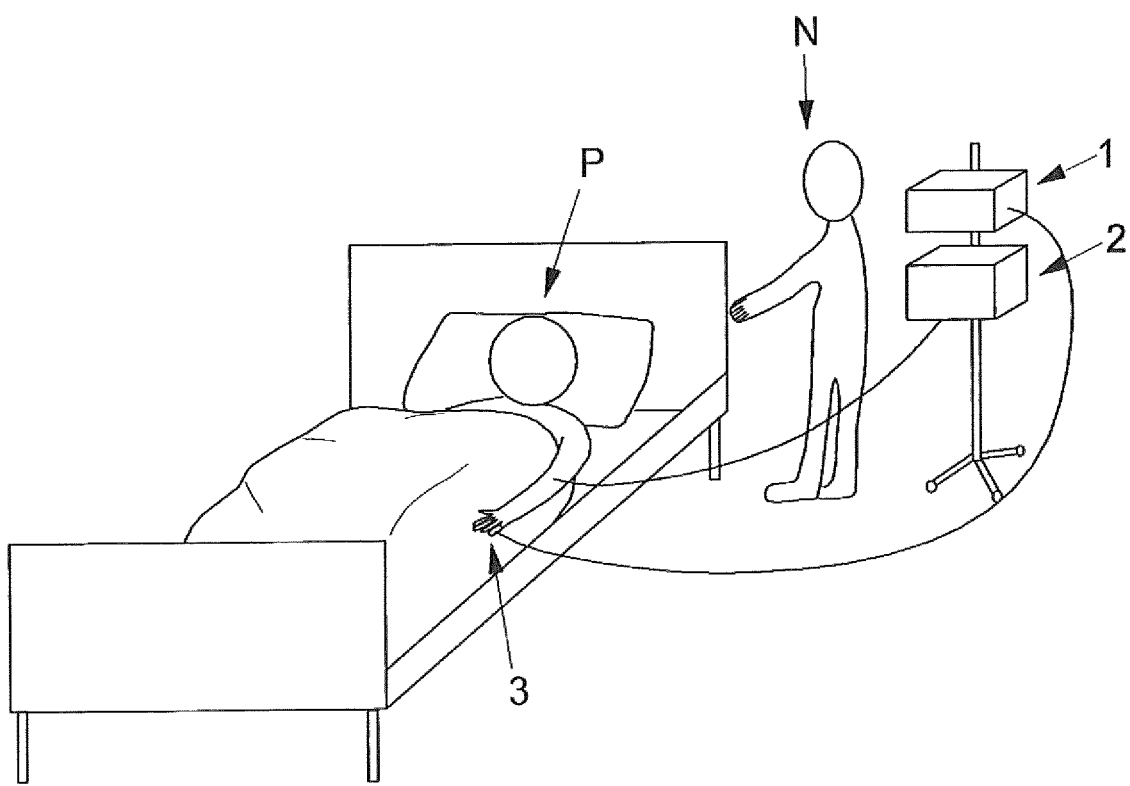
FIG. 1 shows a schematic view of a control device and an infusion pump located at the bedside of the patient.

FIG. 1 shows in a schematic view a typical scenario for example in an intensive care unit (ICU) of a hospital for administering insulin on a continuous basis to critically ill patients. Herein, an infusion pump 2 together with a control device 1 is located for example on a rack at a bedside of a patient P for administering insulin intravenously to the patient P. A nurse N (to be understood generally as a user of the control device 1 and the infusion pump 2; this may also be a physician or the like) operates the control device 1 and the infusion pump 2 and in particular enters control commands to configure and activate an infusion process. A sensor device 3 serves to take blood glucose level measurements on the patient P and for this may be continuously attached to the patient P or may be repeatedly used by the nurse N to take measurements.

The control device 1 serves to control the infusion procedure to be carried out by the infusion pump 2. As depicted in the functional schematic of FIG. 2, the control device 1 comprises a controller 10 which receives as inputs a target glucose level T from a target setting unit 13, an actual blood glucose level G from a sensor device 3 and an actual infusion rate IR from the infusion pump 2, for example a syringe pump. The controller 10, based on such input values, determines a recommended infusion rate R, which is fed to the infusion pump 2 for administering insulin to a patient P.

Figure 2:
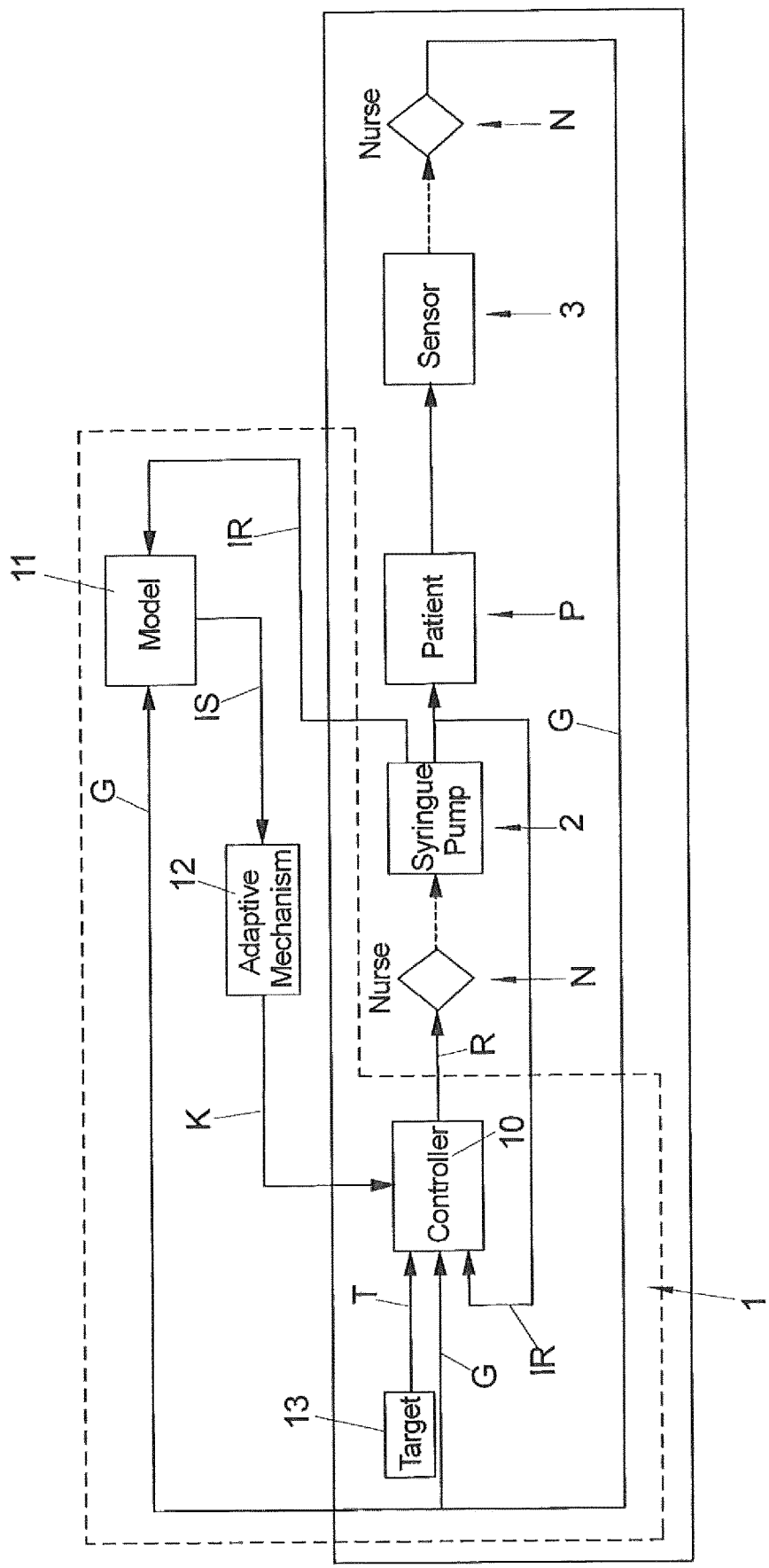
FIG. 2 shows a block diagram of the control device in cooperation with an infusion pump and a sensor device.

In FIG. 2, dashed arrows (between nurse N and the syringe pump 2 and between the sensor device 3 and nurse N) indicate an interaction by a nurse N. In particular, the nurse N is required to confirm the recommended infusion rate R provided by the controller 10 of the control device 1, and only upon approval by the nurse N the infusion pump 2 administers insulin to the patient P using that recommended infusion rate R. The nurse N, in this regard, also has the option to modify the recommended infusion rate R, such that the infusion pump 2, instead of the recommended infusion rate R, uses a different, modified infusion rate IR for administering insulin to the patient P. In the latter case, the recommended infusion rate R and the actual infusion rate IR are different from each other.

The controller 10 is configured as a proportional-integral-derivative (PID) controller. Such controller 10 uses a controller equation having different terms, namely a proportional term, an integral term and a derivative term. With each term a gain is associated, which, in the control device 1 of FIG. 2, is set using a model unit 11 and an adaption unit 12 providing a set of appropriate gains K to the controller 10.

The model unit 11 implements a pharmacokinetic-pharmacodynamic (PkPd) model in which the physical system of a patient is modelled using different compartments relating to different functional systems, such as a plasma compartment, an insulin-distribution compartment and a so called remote compartment.

An example of a suitable model is described by Christopher E. Hann et al., "Integral-based parameter identification for long-term dynamic verification of a glucose-insulin system model", Computer Methods and Programs in Biomedicine (2005) 77, 259-270, which shall be incorporated by reference herein.

By means of such a model the actual infusion rate IR provided by the infusion pump 2 is matched to the actually measured blood glucose level G by adapting two parameters of the model, namely the insulin sensitivity IS and the glucose clearance rate. The model hence can be used to estimate in particular the insulin sensitivity IS of a patient P in a specific state under specific conditions and can provide such insulin sensitivity IS to the adaption unit 12.

In a particular example the model of Hann et al. (see above) was used using the following patient-specific parameters:

BM: Body Mass $V_G$: glucose distribution volume→$V_G$=0.19·BM (kg)

$V_I$: insulin distribution space→$V_I$=0.12·BM (kg)

$I_b$: basal insulin (endogenous production of insulin from the pancreas, equals to 0 for diabetics)→$I_b$=|−2.08+ 0.0352IBW$_R$|$_+$ $G_b$: basal glycaemia (endogenous production of glucose by the liver)

$$G_b = (0.245 + 3.56 \cdot 10^{-3} IBW_R)$$

$$IBW_R = \frac{BMI(\text{body mass index})}{IBW(\text{ideal body weight})}$$

$$BMI = \frac{\text{weight(kg)}}{\text{size}(m)^2}$$

$$IBW = \begin{cases} 0.5 BMI + 11.5 & \text{for men} \\ 0.4\ BMI + 0.03 \cdot \text{Age(years)} + 11 & \text{for women} \end{cases}$$

$G_E$: glycemic equilibrium (blood glucose level at rest, 5.5 mM for healthy, 7.5 mM for diabetics)

Applying the method from Hann et al., the glucose clearance rate $p_G$ and the insulin sensitivity $S_I$ (in this text also referred to as IS) can then be estimated.

The adaption unit 12 serves to convert the insulin sensitivity IS of the patient P provided by the model unit 11 into a set of gains K to be provided to the controller 10. For this, the adaption unit 12 associates the insulin sensitivity IS to a predefined insulin sensitivity class C1-C4, as by way of example shown in FIG. 3. Each insulin sensitivity class C1-C4 herein is associated with a particular set of gains K, which are predefined and represent the gains K corresponding to points lying at centers Z1-Z4 of the different insulin sensitivity classes C1-C4.

Figure 3:
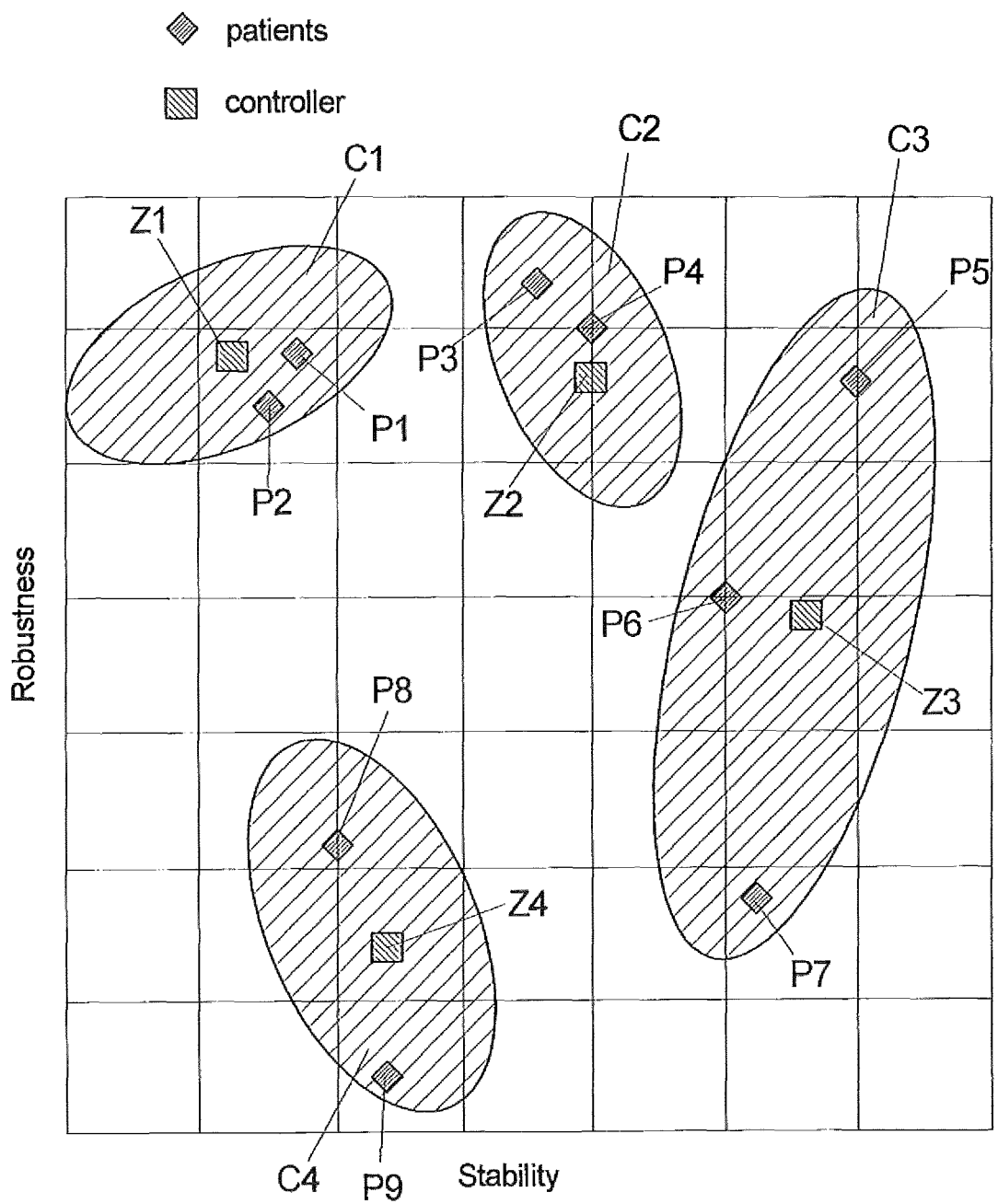
FIG. 3 shows a schematic diagram of different insulin sensitivity classes.

It is to be noted in this regard that FIG. 3 is only a schematic drawing. There actually may be more or less than four classes C1-C4, for example six classes. Of such classes a first number of classes, for example four classes, may be associated with insulin sensitivities IS regularly occurring in patients, and a second number of classes, for example two classes, may be associated with rare insulin sensitivities IS (i.e. extreme values of insulin sensitivity IS). The classes C1-C4 may have a different shape than depicted in FIG. 3 and for example may be adjoining or even overlapping in the stability-robustness plane shown in FIG. 3.

As shown in FIG. 3, the insulin sensitivity classes C1-C4 are defined in a two-dimensional plane, whose axes are spanned by a so called stability parameter and a robustness parameter. Such parameters are defined as follows:

$$\int_0^t |\varepsilon(\tau, S_I, K)| d\tau = H(S_I, K) \qquad \text{Stability parameter:}$$

Herein, $\varepsilon(t, S_I, K) = G(t, S_I, K) - G_{ref}(G(t, S_I, K)$ represents the simulated blood glucose level, wherein G (representing the plasma glucose level above equilibrium) depends on the insulin sensitivity $S_I$ and of the controller gains K. Thus, for a same patient (age, size, weight, diabetes status, gender), changing $S_I$ and/or K will result in different values of the stability parameter $H(S_I, K)$.

$$R(S_I) = \int_0^t |\varepsilon(\tau, S_I, K) - \varepsilon(\tau, S_{I_c}, K)| d\tau \qquad \text{Robustness parameter:}$$

The robustness parameter $R(S_I)$ indicates the robustness for an insulin sensitivity value S, using a PID controller, the gains K of which have been optimized for an insulin sensitivity value $S_{Ic}$ (using constant patient-specific parameters in the model).

The stability parameter and the robustness parameter hence are computed according to the particular insulin sensitivity value, such that with each insulin sensitivity value a pair of one stability parameter and one robustness parameter is associated. This is indicated in FIG. 3 by points P1-P9, which relate to particular insulin sensitivity values IS for specific patients P in a specific states. If the point P1-P9 associated with a particular insulin sensitivity IS falls into the range of a particular class C1-C4, the insulin sensitivity IS is considered to belong to that class C1-C4, and the particular set of gains associated with that class C1-C4 is chosen and provided to the controller 10.

The insulin sensitivity classes C1-C4 are determined in advance such that they are predefined when carrying out an actual insulin administration procedure. The previously constructed insulin sensitivity classes C1-C4 are associated each with a set of particular, appropriate controller gains K, wherein the set of gains K of a particular class C1-C4 is appropriate for all insulin sensitivity values IS belonging to that class C1-C4 in that for all insulin sensitivity values IS of a particular class C1-C4 an acceptable stability and robustness is achieved. The boundaries of a class C1-C4 are herein determined by a threshold beyond which the stability and/or robustness degrade when using the controller gain settings associated with that class, thus yielding a poor controller behaviour.

It is to be understood that FIG. 3 shows only an example of possible insulin sensitivity classes C1-C4. In reality, the entire plane spanned by the stability parameter and the robustness parameter is covered by discrete insulin sensitivity classes C1-C4 such that any insulin sensitivity value IS may be associated with a particular, discrete class C1-C4.

By constructing the insulin sensitivity classes C1-C4 in advance the algorithm can be made particularly efficient, because during runtime no extensive computations need to be carried out. The determination of the controller gains K can simply be achieved by determining into what class C1-C4 a particular insulin sensitivity value IS falls, wherein the gains K are then determined by the particular set of gains associated with that class C1-C4.

Figure 4:
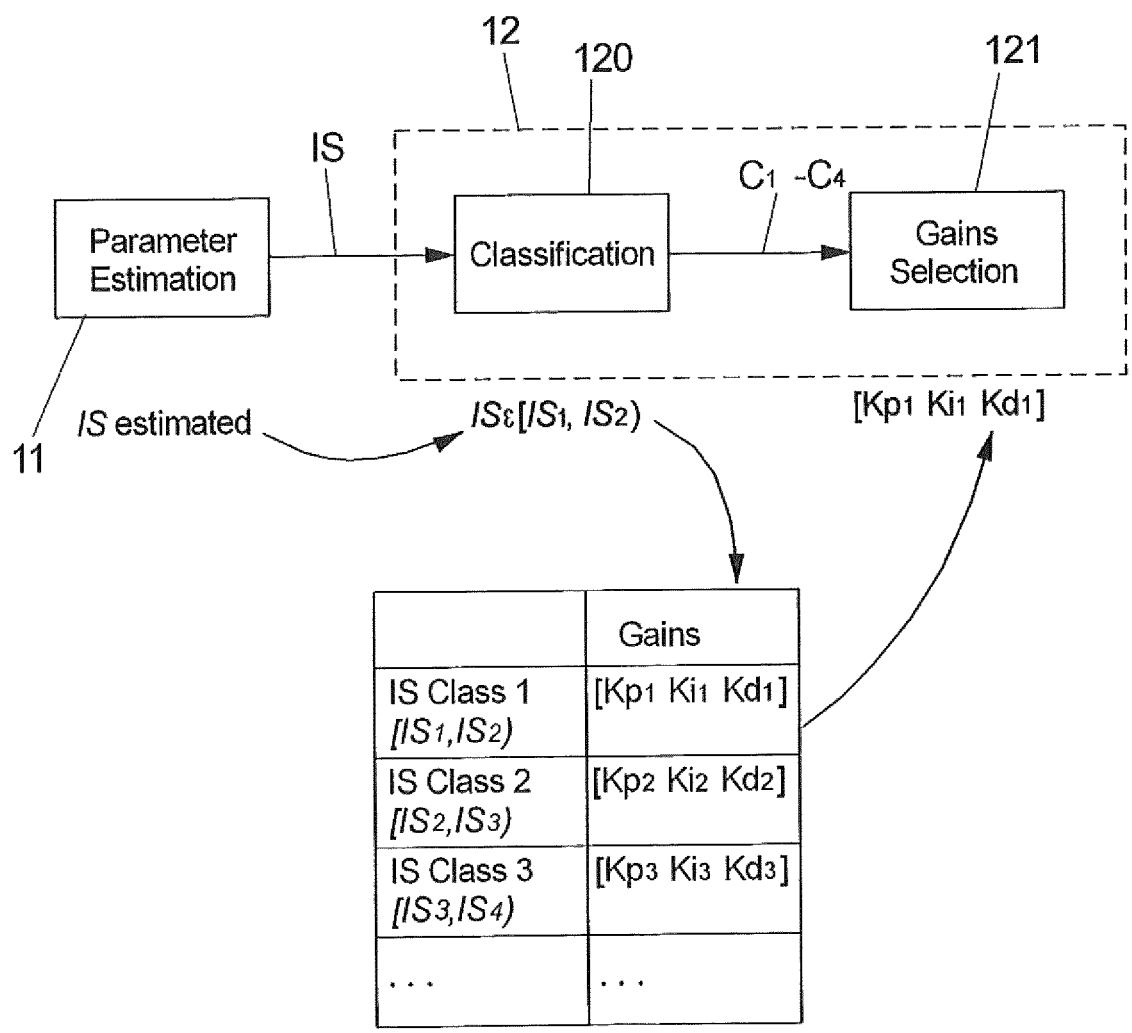
FIG. 4 shows a schematic view of the determination of a set of gains based on an insulin sensitivity of a patient.

The principal procedure for determining the set of gains for an insulin sensitivity IS provided by the model unit 11 is outlined in FIG. 4. The model unit 11 provides the insulin sensitivity IS to the adaption unit 12. Within the adaption unit 12 a classification unit 120 classifies the insulin sensitivity IS by determining the class C1-C4 the insulin sensitivity IS belongs to. With that class C1-C4 a set of gains $K_p$, $K_i$, $K_d$ is associated, together forming the set of gains K. According to the class C1-C4 associated with the insulin sensitivity IS, hence, a set of gains K is determined in a gain selection unit 121 and provided to the controller 10.

The controller 10, as said above, is for example set up as a PID controller using a PID controller equation which may be stated as follows:

$$u(t_n) = K_p(S_{I_n})$$

$$\left( \epsilon(t_n) + \sum_{k=1}^{n} e^{-(n-k)\beta}(t_k - t_{k-1}) \left( \frac{1}{T_I(S_{I_n})} \left( \frac{\epsilon(t_k) + \epsilon(t_{k-1})}{2} \right) + \frac{1}{K_p(S_{I_n})T_t(S_{I_n})} \right. \right.$$

$$(u_{sat}(t_k, G(t_k)) - u(t_k)) + \frac{1}{K_p(S_{I_n})T_c(S_{I_n})}$$

$$\left. \left. (v(t_{k-1}) - u_{sat}(t_{k-1}, G(t_{k-1}))) \right) + \frac{1}{T_d(S_{I_n})} \frac{\epsilon(t_k) - \epsilon(t_{k-1})}{t_k - t_{k-1}} \right)$$

Herein, $\epsilon(t_n)=G(t_n)-G_{ref}$ $K_p(S_{I_n})$, $T_I(S_{I_n})$, $T_d(S_{I_n})$ indicate the gains of the proportional term, the integral term and the derivative term, respectively ($K_i=K_p/T_i$ and $K_d=K_p/T_d$, respectively). $T_t(S_{I_n})$ is a gain parameter of a so-called anti-windup term, which allows to handle saturation constraints. $T_c(S_{I_n})$ is a gain parameter of a compliance term, which allows the controller to take into account modifications to a recommended infusion rate by medical staff for a next recommendation.

Together with the gain parameters $T_t$ (for the anti-windup term) and $T_c$ (for the compliance term) hence a set of five gains $K_p$, $K_i$, $K_d$, $T_t$, $T_t$ exists, which together form the set of gains K associated with an insulin sensitivity class C1-C4.

The term $e^{-(n-k)\beta}$ in the equation above is an exponential forgetting term that allows to "forget" past measurements which may be of lesser relevance for an actual recommendation (old measurements have less and less impact on an actual recommendation, because an insulin dose needed to reach a desired target range in general changes fast dependent on the general patient's state). $\beta$ is called the exponential forgetting factor. It is set to consider that relevant glycemic data generally lie within approximately the last 24 h.

The PID controller equation takes into account a saturation function $$u_{sat}(t,G)=\text{sat}(u(t),G(t)).$$

The saturation function is a two-dimensional function, which in a first dimension applies a common saturation according to $$u_{sat} = sat(u) = \begin{cases} u_{max}, & \text{if } u > u_{max} \\ u_{min}, & \text{if } u < u_{min} \\ sat'(u, G), & \text{otherwise} \end{cases}$$

and in a second dimension is defined by

Sat'$(u,G)$=interpolate$(Gs,Is,G)$, where Gs=[0 2.2 3.3 5.5 8 10] and Is=[0 0 4 8 12 15]. The Interpolate function performs cubic interpolation between data [Gs, Is] and holds the maximum value of Is (i.e. 15 UNITS/h) above Gs=10 mmol/L. The saturation function hence depends on the blood glucose level G. The saturation function serves on the one hand to make sure that the recommended infusion rate output to the infusion pump cannot exceed a predefined maximum value and cannot fall below a predefined minimum value. On the other hand the saturation function depends on the blood glucose level, yielding a higher value $u_{sat}$ for a higher blood glucose level.

The set of gains K are provided to the controller 10 and are being used by the controller 10 in order to determine the recommended infusion rate R based on the target glucose level T, the actually measured glucose level G and the actual infusion rate IR (which matches the previously determined recommended infusion rate R unless the nurse N has modified the infusion rate). Upon administration of insulin to the patient P by means of the infusion pump 2, after some time, for example after half an hour, another measurement of the glucose level G of the patient P is taken by means of the sensor device 3 through the nurse N. The newly measured glucose level G is then again provided to the controller 10 and the model 11 for determining an updated recommended infusion rate R.

Hence, for each measured glucose level G the insulin sensitivity IS for a patient P is determined anew such that changes in the physiological state of the patient P may be tracked and converted to adapt the gain values K. Based on the actual glucose level G and the adapted gains K and taking into account the actual infusion rate R of insulin administered to the patient P the controller 10 then computes the updated recommended infusion rate R for the further administration of insulin to the patient P.

The idea of the invention is not limited to the embodiments described above.

In particular, in principal the model applied by the model unit is not limited to a PkPd model, but may also be another model for determining the insulin sensitivity.

In addition, the controller may have a different shape and may use a different controller equation than the one stated above.

Further, the system described above in principal may also be set up as a closed-loop system which does not require interaction by a nurse. For this, an infusion rate may automatically be sent by the controller to the infusion pump for administration of insulin to the patient, and a blood glucose level measurement may be taken automatically, for example in a periodic fashion at predefined measurement times for providing a feedback to the control device.

Further details about a model used for the method and the control device described above are included in an Appendix attached herewith.

For more details about different embodiments and algorithms embodying the invention it also is referred to the Appendix, which shall form a part of this text.

LIST OF REFERENCE NUMERALS

1 Control device
10 Controller
11 Model unit
12 Adaption unit
120 Classification unit
121 Gain selection unit
13 Target setting unit
2 Infusion pump
3 Sensor
C1, C2, C3, C4 Insulin sensitivity class
G Measured glucose level
IR Infusion rate
IS Insulin sensitivity
K Controller gain
N Nurse
P Patient
P1-P9 Point
R Recommended infusion rate
T Target glucose level
Z1-Z4 Center

APPENDIX

Figure 5:
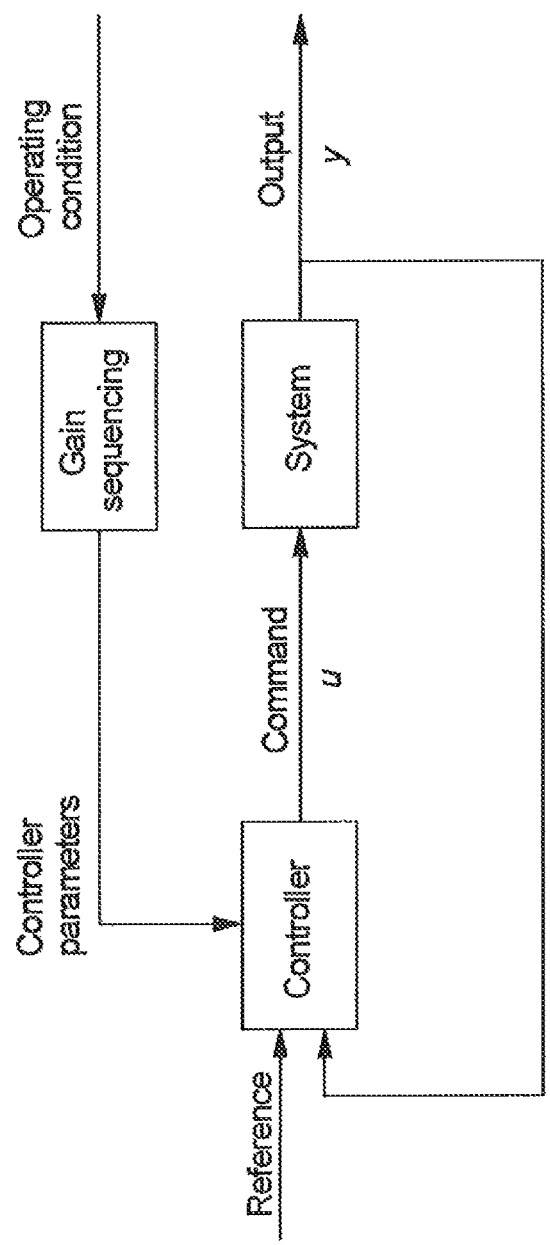
FIG. 5 is a block diagram of a system on which the influence of parameter variation is reduced by gain sequencing

In the appendix it is referred to the following figures:

FIG. 5 Block diagram of a system on which the influence of parameter variation is reduced by gain sequencing.

Figure 6:
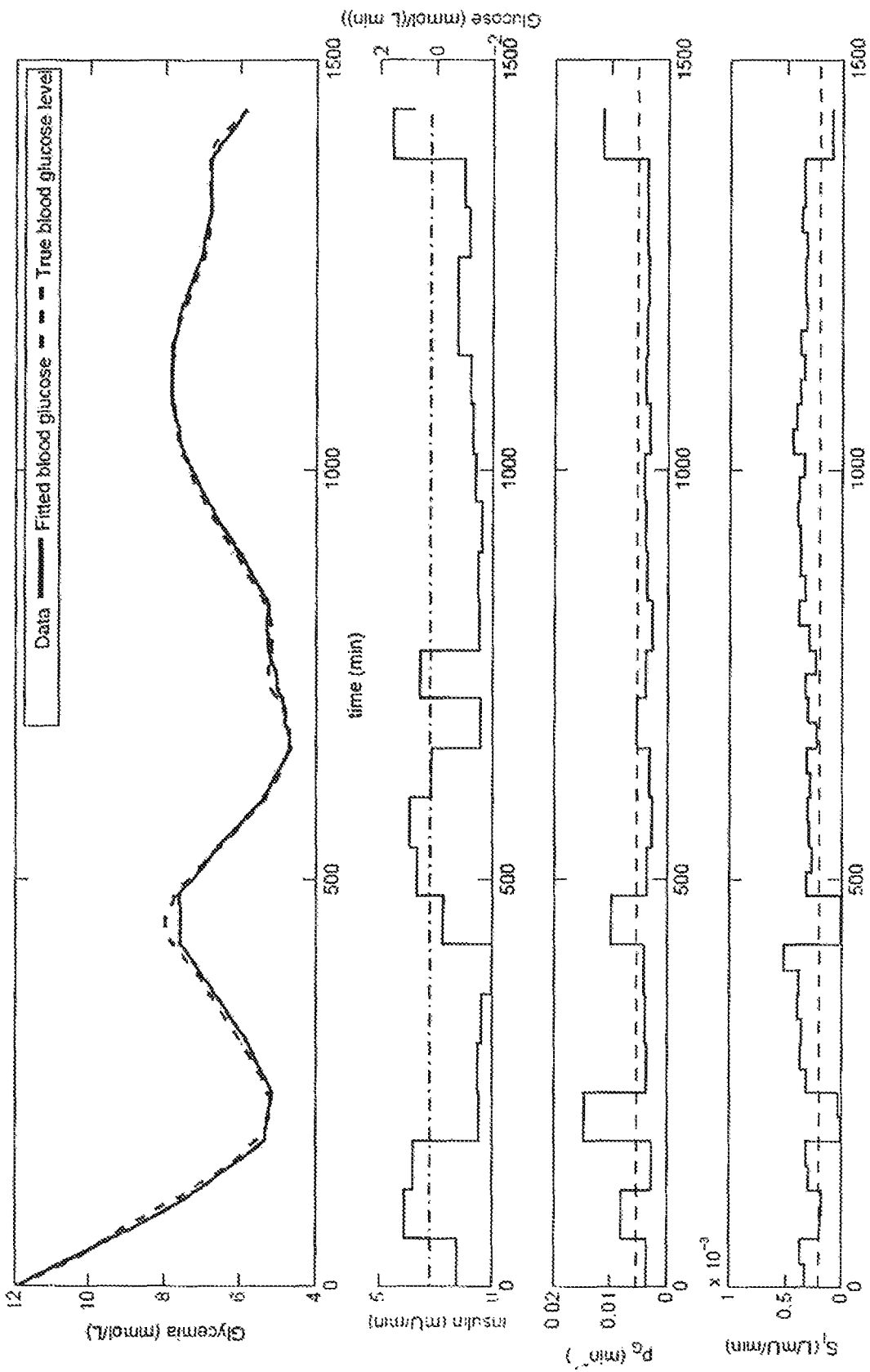
FIG. 6 is a set of graphs illustrating the results of the identification method applied to a simple case.

FIG. 6 Results of the identification method applied to a simple case.

Figure 7:
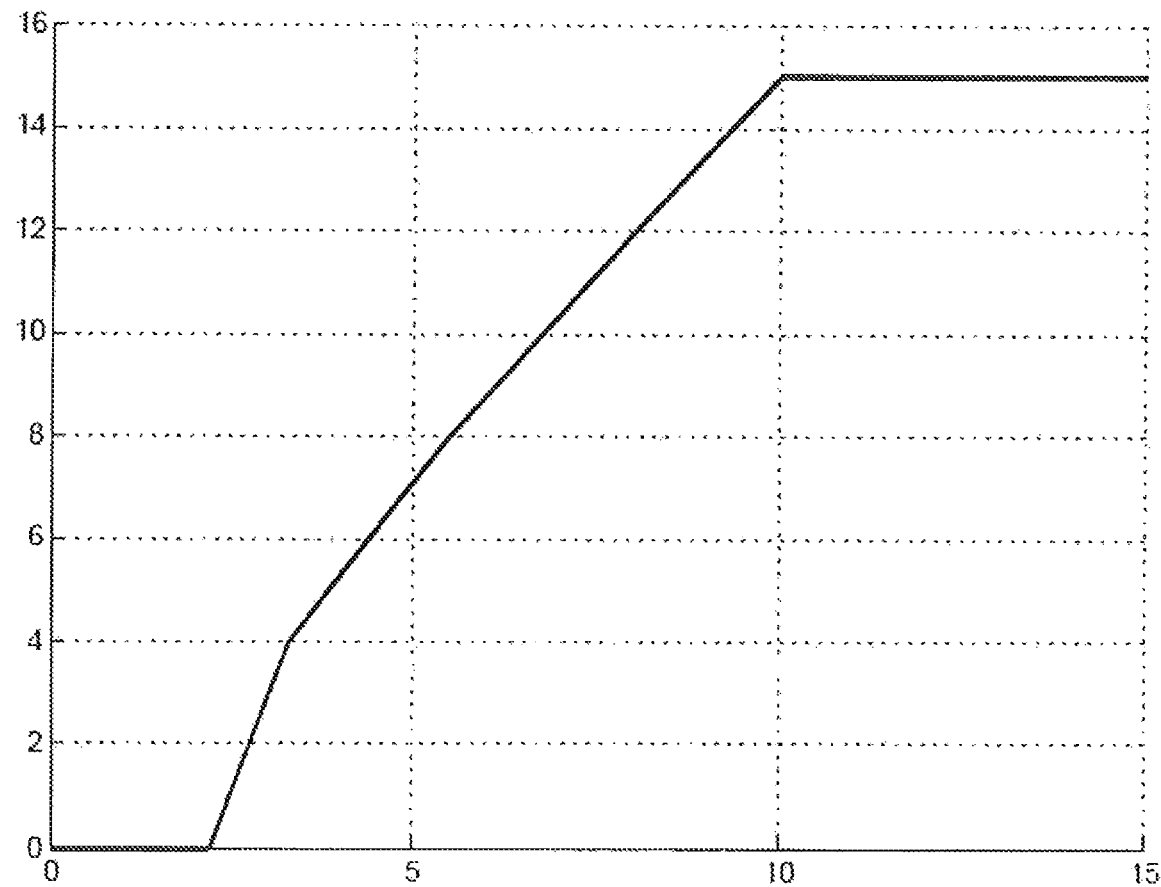
FIG. 7 is a graph of insulin flow rate saturation function according to measured blood glucose.

FIG. 7 Insulin flow rate saturation function according to measured blood glucose.

Figure 8:
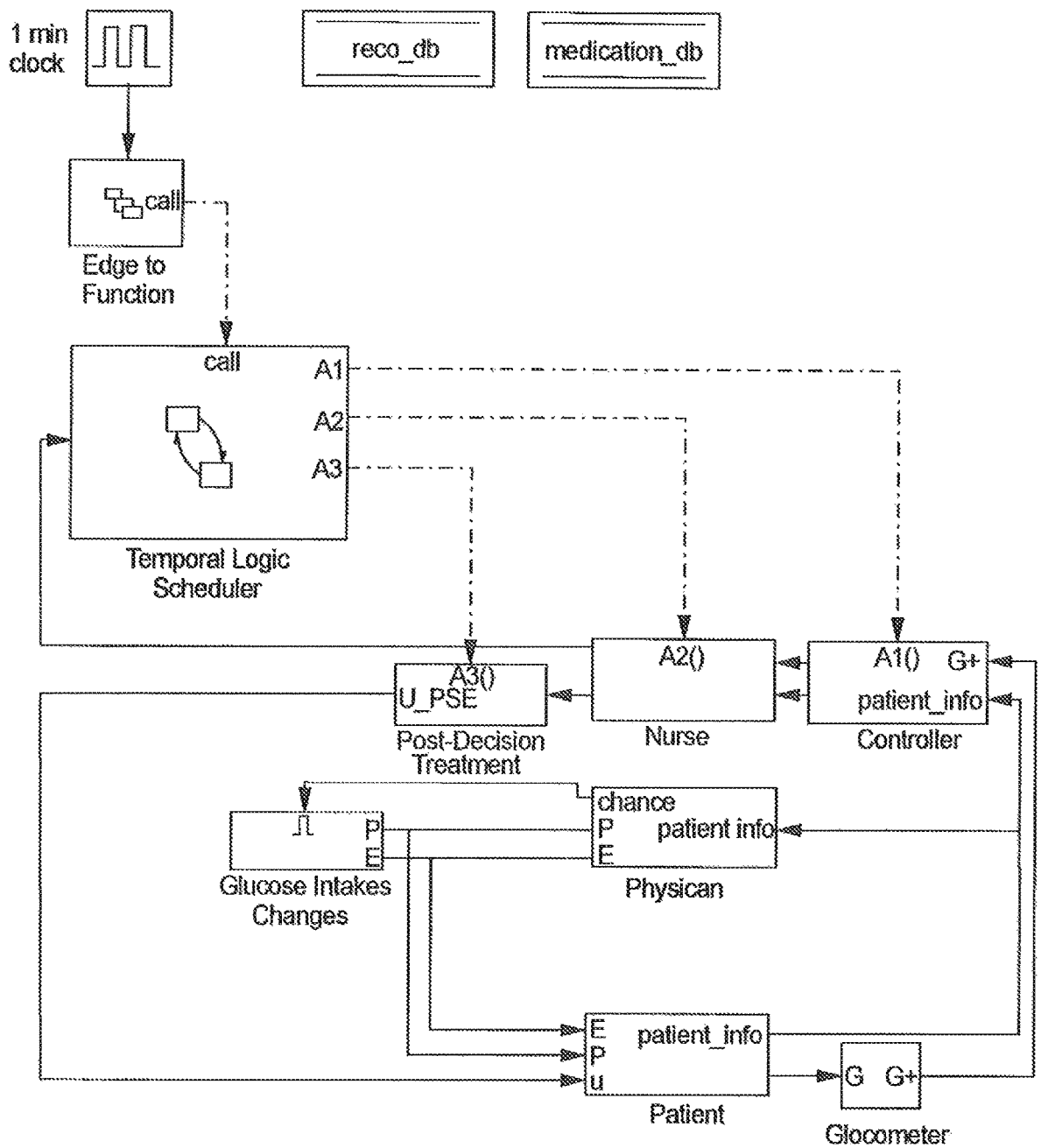
FIG. 8 is a Simulink block diagram of the test bench for the CGAO_v2 algorithm.

FIG. 8 Test bench for the CGAO_v2 algorithm in the form of a Simulink block diagram.

Figure 9:
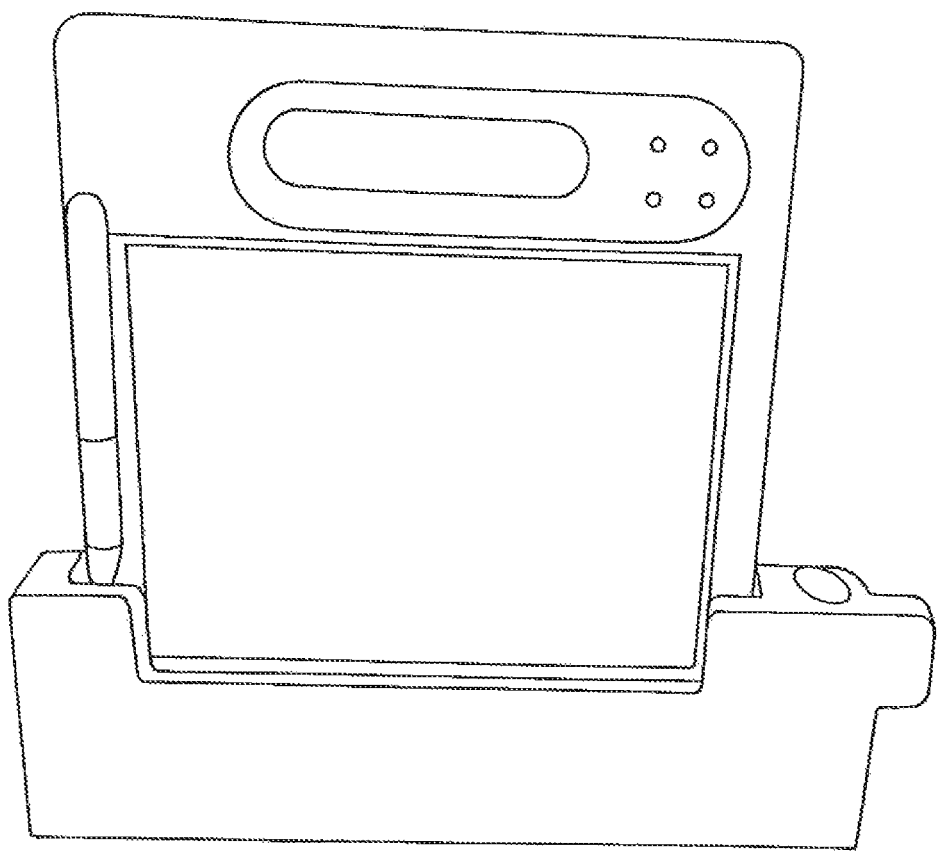
FIG. 9 is a perspective view of a CGAO v2 (master GC™) main user interface screen.

FIG. 9 CGAO v2 (master GCTM) main user interface screen.

Figure 10:
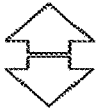
FIG. 10 is a blood glucose measurement entry screen of the CGAO v2 user interface (master GC™).

FIG. 10 Blood glucose measurement entry screen of the CGAO v2 user interface (master GCTM).

Figure 11:
FIG. 11 is a recommendation screen of the CGAO v2 user interface (master GC™).

FIG. 11 CGAO v2 user interface recommendation screen (master GCTM).

Figure 12:
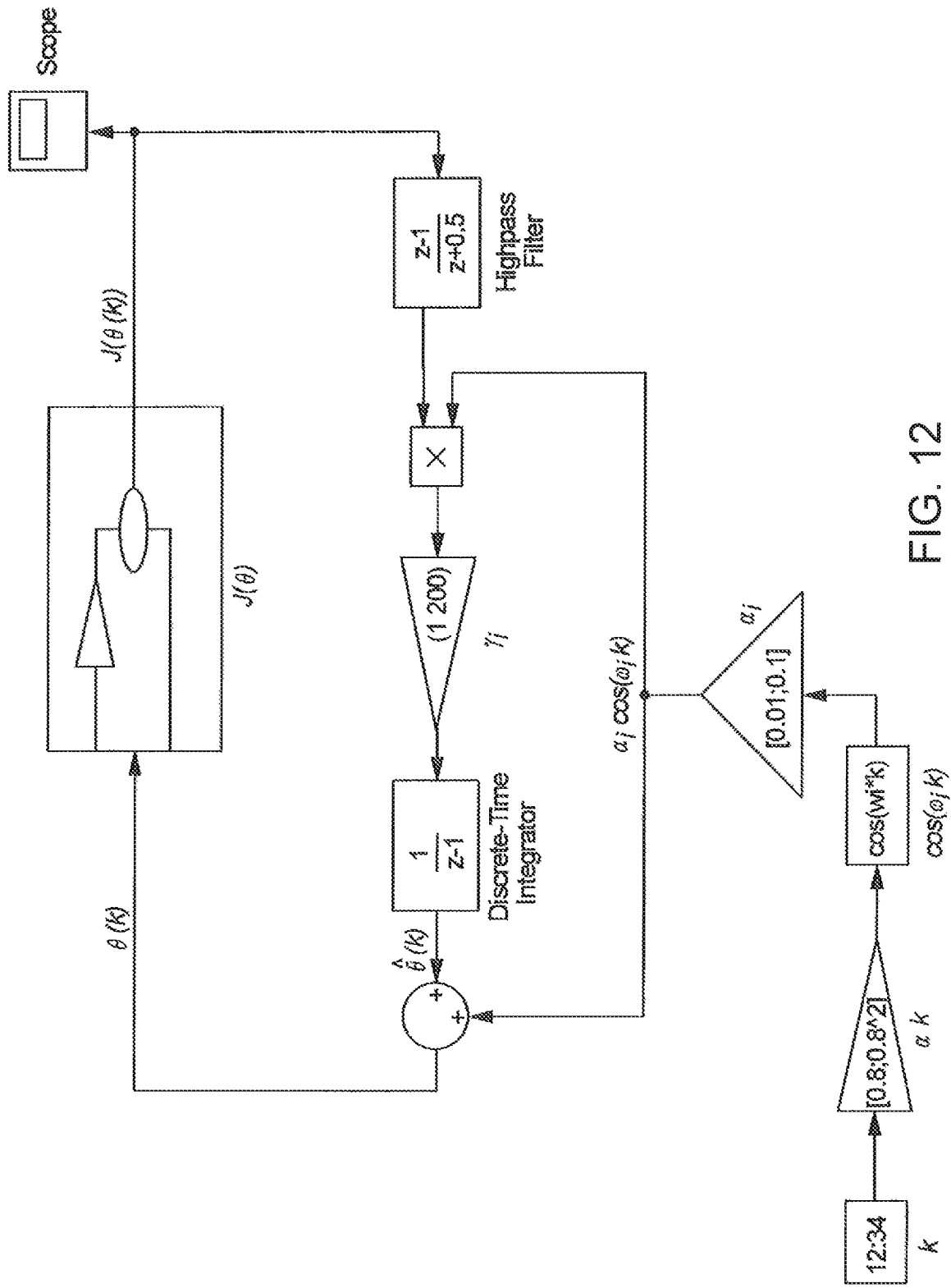
FIG. 12 is a discrete-time block diagram of the ES method.

FIG. 12 Discrete-time block diagram of the ES method.

Figure 13:
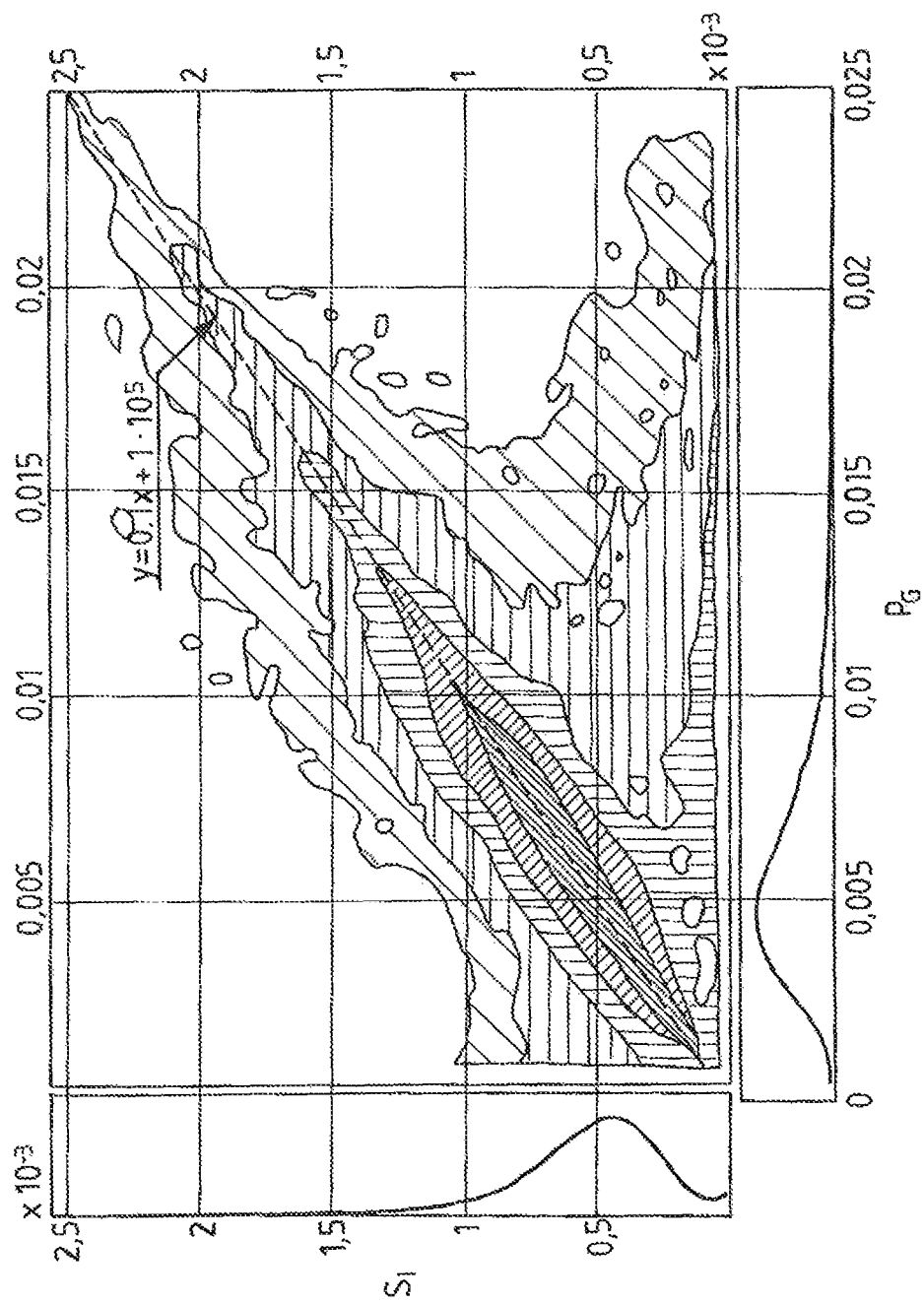
FIG. 13 is a 3D representation of the empirical distributions of the identified $\hat{S}_I$ and $\hat{P}_G$ parameters.

FIG. 13 3D representation of the empirical distributions of the identified $\hat{S}_I$ and $\hat{p}_G$ parameters.

Figure 14:
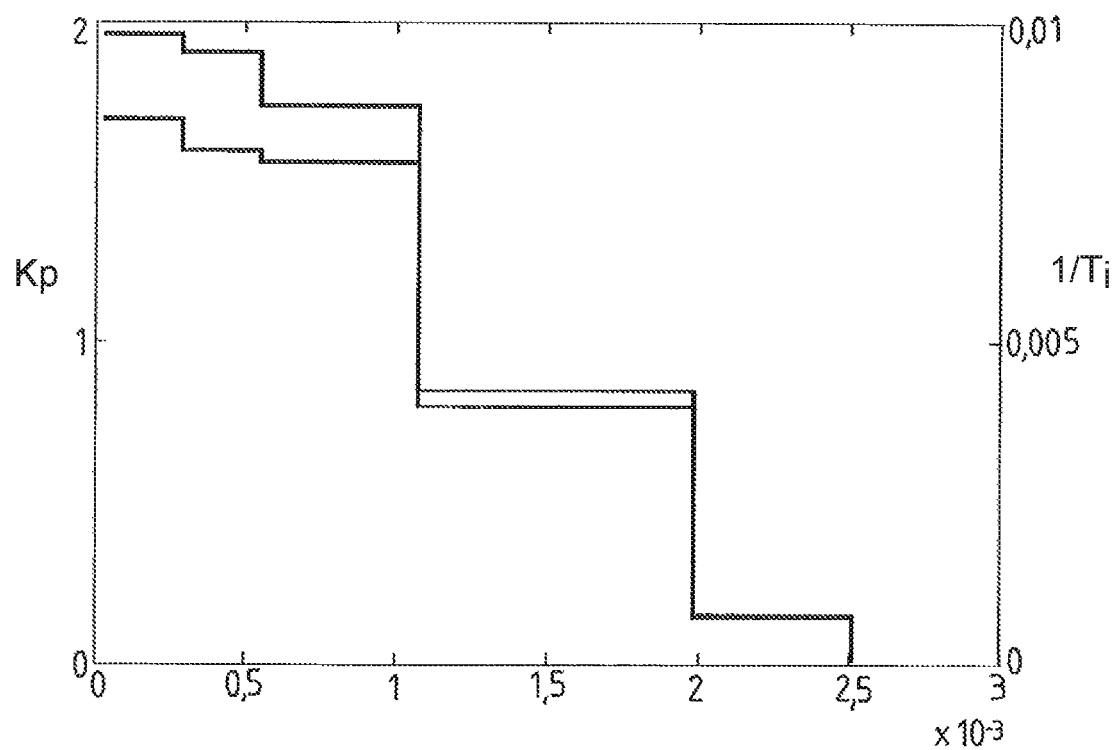
FIG. 14 is a representation of the gain values according to parameter $S_I$.

FIG. 14 Representation of the gain values according to parameter SI.

Figure 15:
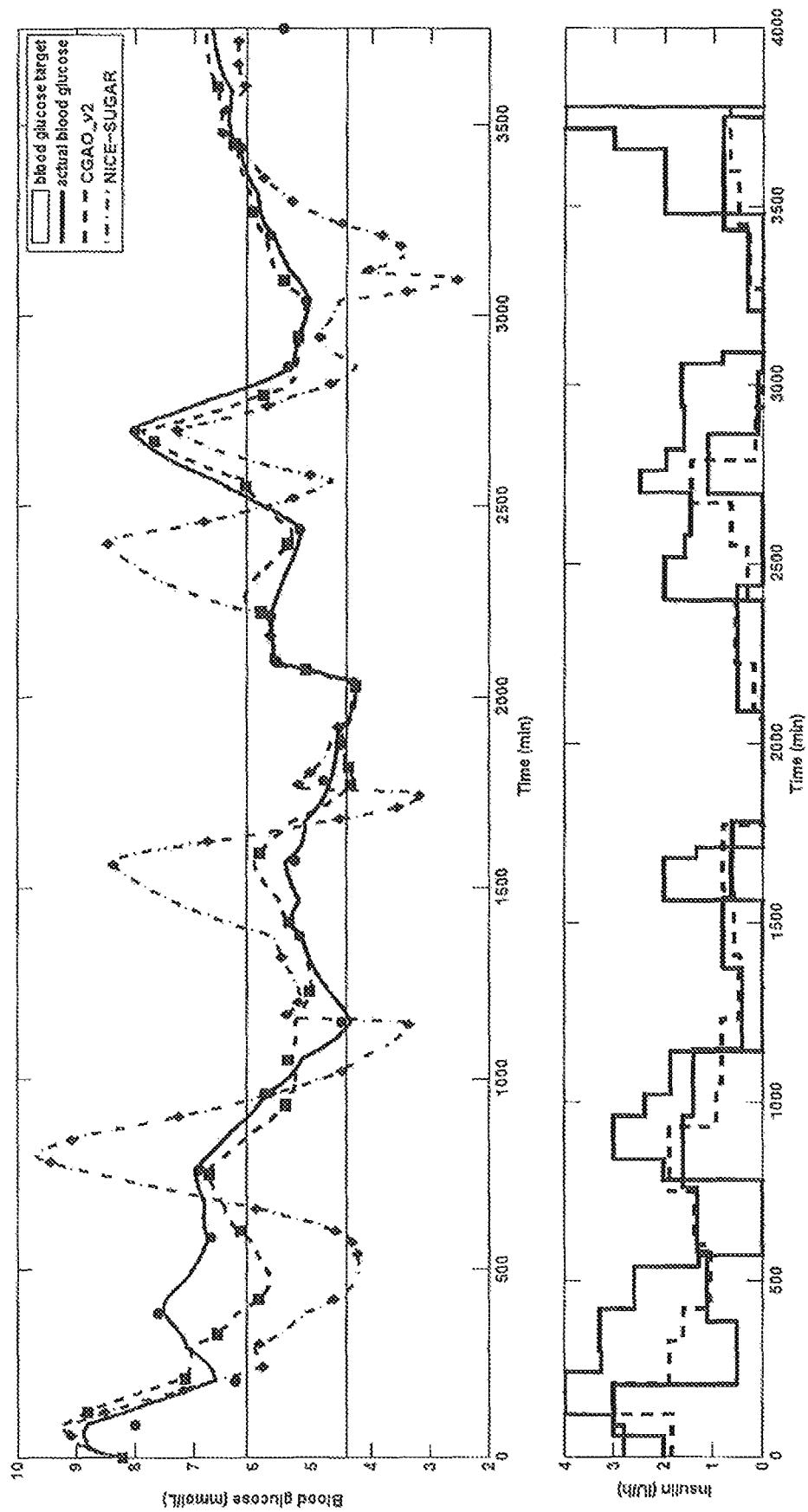
FIG. 15 is an actual scenario of patient 20 of the virtualized CGAO-REA study (solid black curve) reworked using different algorithms: CGAO_v2 (dotted blue curve) and NICE-SUGAR (dot-dash red curve).

FIG. 15 Actual scenario of patient 20 of the virtualized CGAO-REA study (solid black curve) reworked using different algorithms: CGAO_v2 (dotted blue curve) and NICE-SUGAR (dot-dash red curve)

CGAO-v2: A Gain Sequencing Controller

5.1 Introduction

During a study—called the CGAO_REA study—2648 patients were included in 34 French centres for 18 months, of whom 1336 patients received assistance from a controller called CGAO_v1. This corresponds to 15,621 days of use of the controller where more than 110,000 blood glucose measurements (and recommendations) were done in this group alone. The study therefore generated a large quantity of data for using the controller which will prove useful for analysing the algorithm performance. This chapter gives details of the techniques used for exploiting the study data to evaluate the performance of the CGAO_v1 algorithm as well as solutions proposed to improve control in order to provide recommendations that are more personalized and therefore better "adjusted" for each situation. Therefore we will define these methods of adjustment in view of the substantial inter-patient variability as well as intra-patient variability observed after explaining one of the possible origins of this variability and its impact on control in the next section.

The consequent mass of data generated by the study will permit identifying the various blood glucose behaviours defining glycaemic variability. Indeed, each patient responds differently to the same quantity of insulin injected into them, according to the treatments that they receive and the severity of their condition, as well as according to intrinsic parameters such as weight, height, age and diabetic status. From the automation point of view, if we refer to the L and T Ziegler-Nichols parameters used to regulate the controller, a change in the patient's intrinsic parameters corresponds to a change in the model parameters and therefore to a change in the dose response (of which the step response is a specific case). Given that the L and T parameters are directly linked to this response, this means that a change in the patient parameters directly changes the value of the controller gains. If the changes are fairly minor so as not to lead to a significant change in the settings, the PI controller is fairly robust, so that its performance is not affected. On the contrary, if the patient gets worse or better to the point of significantly changing their metabolic parameters, the performance of the controller can degrade to the point of becoming unstable in some extreme cases.

5.2 Benefits of a Controller with Gain Sequencing

Adaptive control is not the solution to all control problems. There are alternatives, one of which is specifically discussed in this section. This method consists of an open-loop change or adaptation of the regulator parameters. In some cases, it is possible to know how the dynamics of a system evolve with the operating conditions of this system. One source of change of the system dynamics may be, for example, well-known nonlinearities. It is then possible to change the controller parameters by monitoring the system operating conditions. This idea is called gain sequencing because it was originally used to adapt to changes of the system gains alone. Gain sequencing is a somewhat special type of nonlinear feedback. It has a linear regulator whose parameters are changed in a pre-programmed manner depending on the system operating conditions.

In our case, the main source of change of the glucose-insulin system nonlinear dynamics during an ICU stay is the administration of drugs such as diuretics, corticosteroids or steroids. These treatments can be likened to different operating conditions since they interfere with the insulin response of glucose metabolism, accentuating the insulin resistance phenomenon. Insulin resistance appears when, for various reasons, insulin cannot exert its action. This then leads to high concentrations of glucose and insulin, since the body releases more hormone to alleviate the anomaly. Drug administration is not the only cause of increased insulin resistance. Other factors contribute to accentuating this phenomenon, such as obesity, physical inactivity, pregnancy, age or even diabetes, although these factors do not change during the ICU stay and therefore do not change the operating conditions during the stay. In these cases, a simple identification of the time constants of the patient's glucose-insulin system at admission would be sufficient to alleviate this inter-patient variability. However, drug treatments are administered during the stay, depending on the patient's conditions.

Insulin resistance is therefore a time-dependent variable correlated with changes in the glucose-insulin system dynamics caused by the various factors mentioned above (age, height, weight, diabetes, treatments, etc.). It therefore provides indirect measurements of the system operating conditions on which the gain sequencing may be based to compensate for changes in the dynamics of the system concerned. Gain sequencing therefore reduces the effects of variations in the system parameters simply by changing the parameters of the controller according to auxiliary variables correlated with the operating conditions, here insulin resistance. FIG. 5 illustrates this concept. Gain sequencing can consequently be likened to a feedback control system the gains of which are adjusted by feedforward compensation. This open-loop compensation is also one of the disadvantages of control by gain sequencing. There is actually no feedback to correct incorrect sequencing. Therefore special attention is required to determine the controller gain values. They must be determined for many operating conditions and the associated performances must be verified by many simulations.

This is the job which was done by the following using numerous situations identified during the study where patients originate from various intensive care departments (general, surgical, etc.) with different practices or who received various treatment during a variable period, etc. All this information was used to retrospectively determine the intrinsic parameters of patients via those models of the glucose-insulin system pharmacodynamics and enabled working with several thousand scenarios identified during the study.

5.3 Patient Classification Method 5.3.1 Method of Identifying Insulin Resistance Based on Integrals In the preceding section, we explained that the best method to measure the changes in glucose-insulin system dynamics was to estimate insulin resistance. However, insulin resistance cannot be directly measured. One commonly used method is the estimate of insulin resistance using a mathematical model. In particular, the Bergman model (Richard N Bergman, Lawrence S Phillips, and Claudio Cobelli. Physiologic Evaluation of Factors Controlling Glucose Tolerance in Man. J. Clin. Invest., 68 (December 1981): 1456-1467, 1981) gives the best performance during intravenous glucose tolerance tests (IVGTT) with a single glucose administration. The IVGTT consists of injecting a dose of $d_0$=300 mg/kg into a patient for 60 s then taking blood samples of 2 mL at variable time intervals (short at the beginning (2 min for 30 min), then at 5 min, 10 min and up to 20 min after 1.5 h) for 3 h. Glucose injection induces an abrupt increase in blood glucose, then the pancreas releases insulin to bring the blood glucose back to normal. Plasma glucose and insulin concentration are determined from blood samples. The minimal model coefficients are then estimated working with measured blood glucose data so that the model predicts the same decrease of plasma glucose when insulin (measured) is secreted. It is therefore possible to calculate the insulin resistance index from the model parameters ($P_3/P_2$).

It is obvious that such a study cannot be done routinely on ICU patients. However, based on the same principle, it is possible to determine an insulin resistance index from (known) patient input, i.e., glucose intake and insulin administered. Furthermore, the Bergman minimal model is not suited to routine use. The Van Herpe minimal model was modified precisely for routine use for ICU patients. However, the current methods used for identifying the parameters are nonlinear, non-convex and, in some cases, have calculation times that are too long to be used in real time in the majority of clinical environments (Ewart Carson and Claudio Cobelli. Modelling Methodology for Physiology and Medicine. Academic Press, London, 2000). In this part, we will use a parameter identification technique based on the integrals developed by Hann et al. (Christopher E Hann, J Geoffrey Chase, Jessica Lin, Thomas Lotz, Carmen V Doran, and Geoffrey M Shaw. Integral-based parameter identification for longterm dynamic verification of a glucose-insulin system model. Computer methods and programs in biomedicine, 77(3): 259_70, March 2005) from the Wong model already discussed. The Wong model, moreover, directly results from this technique where Hann et al. reformulated a glucose-insulin system model for patients in intensive care in terms of integral whose nonlinear control analysis was performed by Kovacs et al. (Levente Kovács, Péter Szalay, Balárs Benyó, and J Geoffrey Chase. Nonlinear Control Analysis of an ICU Model for Tight Glycaemic Control. In 18th World Congress of the International Federation of Automatic Control (IFAC 2011), page 6 pp. University of Canterbury. Mechanical Engineering, 2011). A fast and precise identification method is important in a process where the controller relies on the estimate of a parameter to regulate its gains. Regarding nonlinear or non-convex methods, the error may be due to the model not capturing certain dynamics or finding a local minimum instead of a global minimum. Methods using different starting points may provide better results at the cost of longer calculation times. However, there is still a probability of finding the global minimum while convex methods allow it to be found with certainty.

Moreover, the use of the Wong model has several advantages with regard to the Van Herpe minimal model beyond the real-time insulin resistance identification method. Indeed, although they are both based on the Bergman model, the Wong model integrates more complex phenomena such as the saturation of insulin receptors limiting the effect of insulin at a certain concentration limit and the saturation of the insulin disappearance dynamics. The hepatic glucose production term when blood glucose exceeds a certain limit was ignored since this response is inhibited during hyperglycaemic stress observed in ICU patients. It is written as follows:

$$\dot{G} = -p_G G - S_I(G + G_K)\frac{Q}{1 + \alpha_G Q} + \frac{P(t) + P_{end}}{V_G} \quad (5.1)$$

$$\dot{Q} = -kQ + kI \quad (5.2)$$

$$\dot{I} = -\frac{nI}{1 + \alpha_I I} + \frac{u(t)}{V_I} + e^{-u(t)}\frac{I_{end}}{V_I} \quad (5.3)$$

where G and I represent the glucose concentration above the level of equilibrium $G_E$ (mmol/L), and the plasma insulin concentration linked to the input of exogenous insulin (mIU/L), respectively. Q is the distant compartment representing the delay of the action of insulin on glucose (mU/L). P is the input of exogenous glucose (mmol/min). $I_{end}$ and $P_{end}$ are respectively the production levels of insulin (mU/min) and endogenous glucose (mmol/min), $V_I$ the estimate of the insulin distribution volume (L) determined as a function of patient weight (kg), $V_G$ the glucose distribution space (L) determined as a function of patient BMI (kg/m$^2$) and ideal weight (kg), n the degree of insulin suppression, e.g. by the kidneys (min$^{-1}$), k the insulin half-life parameter (min$^{-1}$) and $\alpha_G$ and $\alpha_I$ the Michaelis-Menten parameters for saturation of glucose absorption by the cells (L/mU) and insulin transport (L/mU), respectively. $p_G$ and $S_I$ are patient-specific parameters, variable over time and which represent endogenous glucose absorption (min$^{-1}$) and insulin sensitivity, i.e. the inverse of insulin resistance (L/mU/min), respectively. Finally, u(t) is the input of exogenous insulin (mU/min).

Several minor modifications were introduced compared to the original model. The terms for endogenous insulin and glucose production were added and the values were taken from the relations established by Van Herpe (Tom Van Herpe, Marcelo Espinoza, Niels Haverbeke, Bart De Moor, and Greet Van den Berghe. Glycemia Prediction in Critically Ill Patients Using an Adaptive Modeling Approach. Journal of diabetes science and technology, 1(3): 348_356, 2007) with the ideal weight relative index and converted to the right units. They are expressed as follows:

$$P_{end} = (0.245 + 3.5610^{-3} IPI_R), \quad (5.4)$$

$$I_{end} = |-2.08 + 0.0352 IPI_R|_+, \quad (5.5)$$

where $IPI_R$ is the ideal weight relative index and represents the ratio between actual weight and ideal weight. That is:

$$BMI = weight(kg)/(height(m))^2, \quad (5.6)$$

$$\text{Male: } BMI_{Ideal} = 0.5 \cdot BMI + 11.5 \quad (5.7)$$

$$\text{Female: } BMI_{Ideal} = 0.4 \cdot BMI + 0.03 \cdot Age + 11 \quad (5.8)$$

$$IPI_R = BMI/\text{ideal BMI} \quad (5.9)$$

Likewise, the glucose distribution space $V_G$ and the insulin distribution volume $V_I$ are a function of the patient weight through the relationships $V_G = 0.16 \cdot$weight (kg) and $V_I = 0.12 \cdot$weight (kg). The term for suppression of endogenous insulin production $e^{-u(t)}$ observed in normal individuals and healthy diabetics is not effective in ICU patients. Consequently, the term $e^{-u(t)} I_{end}$ can be reduced to a constant $I_{end}$. The remaining parameters $\alpha_G$, $\alpha_I$, n, k are considered constant and were set at the mean population values (Christopher E Hann, J Geoffrey Chase, Jessica Lin, Thomas Lotz, Carmen V Doran, and Geoffrey M Shaw. Integral-based parameter identification for longterm dynamic verification of a glucose-insulin system model. Computer methods and programs in biomedicine, 77(3): 259_70, March 2005). They are listed in Table 5.1.

TABLE 5.1

Description of the parameters used in the Wong model

| State variable | Unit | Description | |
|---|---|---|---|
| G | mmol/L | Plasma glucose concentration | |
| Q | mU/L | Insulin concentration associated with interstitial sites | |
| I | mU/L | Plasma insulin concentration | |

| Parameter | Unit | Description | Value |
|---|---|---|---|
| $p_G$ | 1/min | Glucose elimination rate | 0.006 |
| $S_I$ | L/mU/min | Insulin sensitivity | 2.25e-4 |
| $\alpha_G$ | L/mU | Insulin effect | 1/65 |
| $\alpha_I$ | L/mU | Disappearance of plasma insulin | 0.0017 |
| $V_G$ | L | Glucose distribution volume | 0.16 Weight (kg) |
| $V_I$ | L | Insulin distribution volume | 0.12 Weight (kg) |
| $P_{end}$ | mmol/min | Endogenous glucose production | (see Eq. 5.4) |
| $I_{end}$ | mU/min | Endogenous insulin production | (see Eq. 5.5) |
| k | 1/min | Insulin half-life | 0.0198 |
| n | 1/min | Insulin disappearance time constant | 0.16 |

Then, by integrating both sides of equation (5.1) and defining $\bar{Q} = Q/(1 + \alpha_G Q)$, the following expression is valid for any segment from $t_0$ to t:

$$\int_{t_0}^{t} \dot{G} dt = \int_{t_0}^{t} \left( -p_G G - S_I (G + G_E) \bar{Q} + \frac{P(t) + P_{end}}{V_G} \right) dt \quad (5.10)$$

$$\Rightarrow G(t) - G(t_0) =$$

$$-\int_{t_0}^{t} p_G G dt - \int_{t_0}^{t} S_I (G + G_E) \bar{Q} dt + \int_{t_0}^{t} \frac{P(t) + P_{end}}{V_G} dt$$

By substituting the total glucose level $G_T = G + G_E$ into equation (5.10) we obtain an equivalent equation easy to calculate from measured total blood glucose:

$$G_T(t) - G_T(t_0) = \quad (5.11)$$

$$-\int_{t_0}^{t} p_G (G_T - G_E) dt - \int_{t_0}^{t} S_I G_T \bar{Q} dt + \int_{t_0}^{t} \frac{P(t) + P_{end}}{V_G} dt$$

In order to reduce the complexity of the calculation and take into account the variation in time, the total time interval was divided into equal segments during which $p_G$ and $S_I$ are defined as piecewise constant:

$$p_G = \sum_{i=1}^{N} p_{G_i} (H(t - t_{i-1}) - H(t - t_i)) \quad (5.12)$$

$$S_I = \sum_{i=1}^{N} S_{I_i} (H(t - t_{i-1}) - H(t - t_i)) \quad (5.13)$$

where $H(t - t_0)$ is the Heaviside function defined by $$H(t - t_0) = \begin{cases} 0 & \text{when } t < t_0 \\ 1 & \text{when } t \geq t_0 \end{cases} \quad (5.14)$$

The value N for equations (5.12) and (5.13) differs according to the time considered per segment. In our case, the time interval between two measurements was variable and unknown in advance, it is the N value that was set in advance rather than the size of the segments as is done in the Hann et al. article. The absorption of glucose by the cells $p_G$ was therefore considered to be constant throughout the time interval considered while insulin sensitivity S, varied once during the time interval between measurements, thus creating time-variable parameters by piecewise constant.

The only unknown parameters of equation (5.11) are therefore $p_{Gi}$ and $S_{Ii}$ defined equations (5.12) and (5.13). However, these parameters are constants as such after having numerically integrated the data; equation (5.11) can be rewritten as a simple linear system according to these two parameters:

$$A \begin{pmatrix} p_{G_i} \\ S_{I_i} \end{pmatrix} = b \tag{5.15}$$

where the number of equations, i.e. the number of lines of matrix A, can be arbitrarily chosen by integrating in different time segments. Moreover, to ensure that the $P_G$ and $S_I$ values obtained remain in a physiological value range, constraints are placed on both parameters when solving (5.15).

To calculate the integrals of equation (5.11) over different time segments, the total blood glucose $G_T$ is approximated by a simple linear interpolation between the two points, thus forming a piecewise linear curve $G_{T\text{-}approx}$. In their article, Hann et al. show that the approximation does not affect the fit by using their method. To find the values of the parameters that give the best fit to the blood glucose values measured during time interval $\Delta t$ defined between the two measurements, a number of 6 equations is defined by the general form:

$$G_{T\text{-}approx}\left(t_0 + \frac{\Delta t}{6}i\right) - G_{T\text{-}fit}\left(t_0 + \frac{\Delta t}{6}i\right) = 0, \ i = 1 \ldots 6 \tag{5.16}$$

For example, the first and last equations are written as follows:

$$G_{T_{approx}}\left(t_0 + \frac{\Delta t}{6}i\right) - G_{T_{approx}}(t_0) - \frac{\Delta t}{6}p_{G_1}G_E + p_{G_1}\int_{t_0}^{t_0+\frac{\Delta t}{6}} G_{T\text{-}approx}(t)dt +$$

$$S_{I_1}\int_{t_0}^{t_0+\frac{\Delta t}{6}} G_{T\text{-}approx}(t)\overline{Q}(t)dt - \int_{t_0}^{t_0+\frac{\Delta t}{6}} \frac{P(t) + P_{end}}{V_G} dt = 0$$

$$G_{T_{approx}}(t_0 + \Delta t) - G_{T_{approx}}(t_0) - \Delta t p_{G_1}G_E + p_{G_1}\int_{t_0}^{t_0+\Delta t} G_{T\text{-}approx}(t)dt +$$

$$S_{I_1}\int_{t_0}^{t_0+\frac{\Delta t}{2}} G_{T\text{-}approx}(t)\overline{Q}(t)dt +$$

$$S_{I_2}\int_{t_0+\frac{\Delta t}{2}}^{t_0+\Delta t} G_{T\text{-}approx}(t)\overline{Q}(t)dt - \int_{t_0}^{t_0+\Delta t} \frac{P(t) + P_{end}}{V_G} dt = 0$$

where the integrals are implemented and evaluated numerically using MATLAB. $\overline{Q}$ can be evaluated by solving equation (5.2):

$$Q = k\int_0^t 1(\tau)\varepsilon^{-k(t-\tau)}dt \tag{5.17}$$

The unknowns are $p_{G1}$, $S_{I1}$, and $S_{I2}$. Then we have a least squares system composed of 6 equations and 3 unknowns. This system can then be solved using the MATLAB lsqlin function.

FIG. 6 shows the result of identifying the Wong model parameters. All the parameters were set at the values described in Table 5.1 both for the system and the identification function. Only the parameters $S_I$ and $p_G$ were assumed to be unknown. The values estimated by the $\hat{S}_I$ and $\hat{p}_G$ model are shown by the solid line and the actual $S_I$ and $p_G$ values are shown by the dotted line. The simulated blood glucose measurements then used for identification are represented by crosses. It can be seen that in certain cases, approximation by a piecewise linear curve is not sufficient to estimate the parameters with precision. A cubic approximation could further improve the results.

5.4 CGAO_v2 Software and Algorithm

The CGAO_v2 algorithm incorporates a PI controller with anti-runaway effect. The forced flow shut off safeties recommended during hypoglycaemic episodes were also retained. The main weakness of controller v1 was its lack of performance for very insulin sensitive or highly insulin resistant patients due to unique gains. This weakness was corrected in v2 by adding the function of gain sequencing presented in the preceding sections. Now the controller is written:

$$u(t_n) = \tag{5.18}$$

$$K_p(S_{I_n}) \cdot \Bigg( \epsilon(t_n) + \sum_{k=1}^{n} e^{-(n-k)\beta}(t_k - t_{k-1})\left(\frac{1}{T_i(S_{I_n})}\right)\left(\frac{\epsilon(t_k) + \epsilon(t_{k-1})}{2}\right) +$$

$$\frac{1}{K_p(S_{I_n})T_1(S_{I_n})}(u_{sat'}(t_k) - u(t_k)) +$$

$$\frac{1}{K_p(S_{I_n})T_c(S_{I_n})}(v(t_{k-1} - u_{sat'}(t_{k-1}))) \Bigg)$$

where $K_p(SI_n)$ represents the gain proportional to the insulin resistance dependent regulator, $T_i(S_{In})$ the integration time constant insulin resistance function and $\varepsilon$ the definite error defined as $\varepsilon(t_n)=G(t_n)-G_{ref}$. $T_c(S_{In})$ corresponds to the time constant for the anti-runaway term also involved in gain sequencing. Finally, a compliance term for changes by the nurse was added. $v(t_{k-1})$ corresponds to the last flow validated by the nurse the value of which can be different from the recommended one $u_{sat}(t_{k-1})$ during the last measurement. The term $(v(t_{k-1}-u_{sat}(t_{k-1}))\Delta t$ represents the quantity of insulin administered more or less. In fact, the nurse is considered here as having more information than the system and can therefore in some cases choose not to comply with the recommendation when it is deemed inappropriate to the situation. Consequently, when the nurse decides to administer a higher insulin flow than the recommended one, the compliance term acts as the anti-runaway term and loads the integrator so as to join the nurse's strategy (which is then considered a saturation) with a time constant $T_c(S_{In})$. The gain values are determined in section 5.5.2.

Saturation. Another safety that was added is saturation on the insulin flow dependent on u (see (3.2)) as well as blood glucose G as Table 5.4 shows. The values between the points are interpolated with the Hermite interpolation method (Carl De Boor. A Practical Guide to Splines. Springer, 2001) and the values outside the table are extrapolated by considering the limit values of the area considered, as FIG. 7 illustrates.

Integrator reset. Finally, in order to overcome certain behaviours associated with jumps in the controller gain induced by sequencing, the value of the integrator calculated with the gains preceding the jump is reassessed with the new gains from equation (5.20). In fact, according to (5.18),

TABLE 5.2

| Table | |
|---|---|
| G(t$_n$)(mmol/L) | u$_{sat}$(t$_n$) (U/h) |
| 0 | 0 |
| 2.2 | 0 |
| 3.3 | 4 |
| 5.5 | 8 |
| 8 | 12 |
| 10 | 15 |

$$u(t_{n-1}) = K_P \varepsilon(t_{n-1}) + In(t_{n-1}) \quad (5.19)$$

therefore, $$In(t_{n-1}) = u(t_{n-1}) - K_P \varepsilon(t_{n-1}). \quad (5.50)$$

Moreover, in order to prevent untimely changes in insulin sensitivity class potentially induced by unreported glucose intake or any periodic event temporarily changing the patient's condition (vomiting, bed changes, etc.), the class change is considered to be significant when the class remains identical for three measurements (around 6 h). Furthermore, in the event of a bolus administered to the patient, since the next measurement interval is naturally small, if the value of the integrator is greater than zero, a safety is applied in order to reinitialize its value to zero. This is in order not to restart the insulin too quickly due to the temporary hyperglycaemic effect of the glucose bolus administered.

Test bench. The algorithm diagrammed in Attachment D was implemented in Simulink. In order to test the algorithm, the operating conditions the block diagram of which is shown in FIG. 8 were implemented in Simulink. The block diagram represents the Virtual Patient—Controller—Nurse closed loop and can be likened to an algorithm test bench insofar as the "Controller" block can be replaced by any algorithm.

The "Patient" block has the same inputs as the virtual patient model, i.e. insulin flow F$_I$ and glucose bolus B$_G$ and insulin bolus B$_I$ (u=(F$_I$, B$_G$, B$_I$)$^T$), enteral E and parenteral P glucose administration. The parameters p$_G$ and S$_I$ are recovered in the MATLAB working environment from an initialization script recovering these parameters from virtual patients discussed later in this chapter. They can be constant or variable as a function of time according to needs. The outputs are the measurement of corresponding blood glucose at the first model state variable and the virtual patient demographic information (height, weight, age, sex, balanced blood glucose, diabetes). The "glucometer" block models the measurement error induced by using an ISO 15197:2003 certified capillary blood glucose reader. This standard stipulates that 95% or more of the blood glucose measurement results must not exceed ±15 mg/dL of error compared to the standard method for concentrations below 75 mg/dL and ±20% for blood glucose greater than or equal to 75 mg/dL. The "Controller" block corresponds to the CGAO_v2 algorithm that returns a new recommendation u*(t$_n$)=(F$_I$*(t$_n$), B*$_G$(t$_n$), B*$_I$(t$_n$), t*$_{n+1}$)$^T$ and measurement error to the nurse e(t$_n$). The "Nurse" block models the nurse strategy in the form of a proportional-derivative (PD) controller. That is, the nurse is considered to react as usual with the department's paper protocols, according to the position of the actual measurement compared to the target and according to the blood glucose variation. The adaptive nature of the nurse is represented by a compliance rate r$_c$, with $0 \leq r_c \leq 1$ and by equation (5.21).

$$I_{IDE_n} = I_{IDE}(t_n) = PD(\varepsilon(t_n))$$

$$I_{K_n} = I_K(t_n) = P_I^*(t_n)$$

$$I_{PSE_n} = I_{IDE_n} + r_e(I_{K_n} - I_{IDE_n}) \quad (5.21)$$

where I$_{IDE}$ represents the nurse's flow rate, I$_K$ the recommended flow rate and I$_{PSE}$ the flow rate actually applied to the PSE. If r$_c$=0, then the nurse is non-compliant regarding the recommendation and I$_{PSE}$=I$_{IDE}$. The situation r$_c$=1 represents a completely compliant nurse. Finally a rate $0<r_c<1$ is a hybrid value between the recommended flow rate and the flow rate that the nurse would apply without the influence of the controller. This latter case corresponds to a relatively compliant nurse with regard to the recommendation. Likewise, the nurse may have a strategy for bolus application, even though in the present case the strategies are considered to be identical, as well as a delay regarding the recommended measurement time. Indeed, as happens in the ICU where the nurse's workload is such that measurements are often late, it is also the nurse who chooses the time at which to come back to make the next measurement through time T.

The "Post-Decision Treatment" block corresponds to the saving in the "reco_db" database of the recommendation, integrating any changes by the nurse. The "Controller" block then accesses this information to take into account the flow changes, recover the last value of the integrator, etc., as is actually done via the IHM. The "Physician" block models the doctor's prescription for parenteral and enteral glucose administration. The doctor's prescriptions are applied directly to the patient and recorded in the "medication_db" database through the "Glucose Intake Changes" block. The Stateflow "Temporal Logic Scheduler" module represents the system clock and activates the blocks associated with measurement instants T defined by the nurse. Outside these instants T, the associated blocks are therefore not active and return to the last value calculated when they were, i.e. during the last measurement.

The algorithm is then integrated into the software of the same name, the architecture and ergonomics of which were redesigned for marketing after the clinical trials (the software was subsequently the subject of a takeover by Fresenius Kabi and was renamed master GC™). The workflow was changed to allow the user to more precisely enter glucose intake and any insulin discontinuations in the PSE. The glucose administration entry form was separated from the blood glucose one, unlike version 1. In this way, the user can precisely enter the time for changing a bag and the associated flow rate so that the software determines the glucose that the patient receives. This step is important for estimating its parameters as we could see above. FIG. 9 shows the main software window installed on a medical tablet with, on the left, (band hidden in the picture) customizable insulin resistance and target blood glucose indicators where the doctor does not want to practice strict control. The algorithm then recalculates the centre of the target used for calculating the recommendation. Indications for glucose administration by enteral and parenteral route and by glucose solution bag are found below. The time of the next control is found on the right, calculated by the algorithm as well as the time remaining, the last blood glucose measured and the flow rate of insulin administered to the patient, the times of which can be different if the nurse has chosen to stop the insulin flow without taking a measurement. The window for presenting the recommendation is shown in FIG. 11. Since the recommendation takes into account glucose administration, this must be correctly entered. An HL7 interface with business software, such as Critical Care Clinisoft from General Electric Healthcare based in Chartres, was set up to avoid double entries as much as possible. In order to guarantee the reliability of the data and not overburden the nurse, the bag end dates are determined by the software and automatically cut (in the software) if the information is not entered. FIG. 10 shows the blood glucose entry window (left) preceding the insulin recommendation window. The nurse chooses to accept or change the recommendation. If she chooses to change it, the software will take this into account as described above.

5.5 CGAO_v2 Controller Settings by Patient Class 5.5.1 Gain Estimation Method

Although PID controllers are widespread in the industry, their effectiveness is often limited due to non-optimal settings. Manually setting controller gains is a complicated task that requires optimizing two parameters. There are multiple ways to optimize these parameters and one of them has already been presented in Section 3.3.2. This is the well-known Ziegler-Nichols (Z-N) technique, which can be implemented quickly and in a simple manner. However, it has also been shown that low measurement sampling frequency significantly degrades control with Z-N settings and this can even destabilize the system in certain cases. To remedy this, the Z-N technique was coupled with a least squares minimization method to refine the gain settings.

In this section, we consider a less complex method of searching for extrema (Extremum Seeking (ES)) (Nick Killingsworth and Miroslav Krsti. Auto-Tuning of PID Controllers via Extremum Seeking. In American Control Conference, pages 2251-2256, 2005) (faster in terms of calculation time), more suited to setting gains in the presence of saturation and roughly equal in performance to the preceding method. The performances are discussed in (Miroslav Krstiã. Performance improvement and limitations in extremum seeking control. Systems & Control Letters, 39: 313-326, 2000) and stability analysis for nonlinear systems is discussed in (Miroslav Krstic and Hsin-hsiung Wang. Stability of extremum seeking feedback for general nonlinear dynamic systems. Automatica, 36: 595-601, 2000), (V Garg, R Kumar, F Lin, S I Marcus, S Lafortune, and G Meyer. Extremum Seeking Control for Discrete-Time Systems. Nasa Technical Memorandum, 47(2): 318_323, 2002) and (Kartik B. Ariyuk and Miroslav Krstic. Real-Time Optimization by Extremum-Seeking Control. John Wiley & Sons, Inc., Hoboken, N.J., 2003). The ES method minimizes a cost function, serving to quantify the performance of the PI controller and similar to the one used previously, so that the output of the cost function reaches a local minimum. The cost function is evaluated at the end of a step response experiment by integrating the squared error:

$$J(\theta) \triangleq \frac{1}{T-t_0}\sum_{t_0}^{T} e^2(t,\theta)dt \qquad (5.22)$$

where the error $\varepsilon(t,\theta) \triangleq y(t,\theta) - r(t)$ represents the difference between the output signal of the looped system and the reference, and $\theta \triangleq [K, T_i]$ the parameters of the PI controller. Setting $t_0$ at the approximate time where the step response of the closed loop system reaches the first peak can set up a zero weight for the initial transition portion of the closed loop system. This allows the start transition not to be constrained and prevents blood glucose variations that are too abrupt and insulin flow rates that are too high.

The ES function the block diagram of which is shown in FIG. 12 was implemented in Simulink. It performs the optimization by disrupting the system input parameters $\theta(k)$ with a sinusoid signal then by estimating the $\nabla J(\theta(k))$. k represents the $k^{th}$ step response experiment. The gradient is determined by filtering the signal $J(\theta(k))$ with a high pass filter to remove the offset then by demodulating and multiplying it by a discrete-time sinusoid of the same frequency. The gradient is then used to modify the entry parameters for the next iteration. In fact, the estimated gradient is integrated with a step $\gamma$ giving the new estimate $\hat{\theta}(k)$. The integrator provides the adaptation function while acting as a low-pass filter.

5.5.2 Determining Patient Classes

Definition. The insulin resistance classes $C_1, C_2 \ldots, C_p$ were then established by first finely discretizing the range of all the physiological insulin sensitivity values $\Omega$, so that:

$$\forall S_{I_i} \varepsilon \Omega, S_{I_{i+1}} = S_{I_i} + h, i=1,\ldots,q$$

and $$\text{span}\{\Omega\} = \text{span}\{S_{I_1}, S_{I_2}, \ldots, S_{I_q}\}$$

where h is the discretization step. Once h is set to be fairly small, the gains $\theta(S_{Ij}) = (K_{pj}, T_{ij})$ associated with each $S_{Ij}$ value are calculated, using the setting method proposed previously. In order to guarantee high controller performances, an insulin sensitivity class $C_k$ is defined by the following properties:

1. $C \subset \Omega$:
2. $C \neq \theta$:
3. $\exists S_{I_n} \varepsilon C$ such that $\forall S_{I} \varepsilon C$, $J(S_{I}, \theta(S_{I_n})) < \varepsilon$ or $J(S_{I}, \theta(S_{I_n}))$ represents the cost function defined in (5.22) and where the dependence with the insulin sensitivity parameter was explicitly added to facilitate writing.

From this definition, p classes of insulin resistance could be determined so that:

$$C_i \cap C_j = \theta, \forall i \neq j:$$

$$U_{k=1}^{p} A_k = \Omega.$$

Application. The set $\Omega$ of $S_I$ values considered for the operating ranges was determined from empirical distributions of physiological values of identified parameters $\hat{p}_G$ and $\hat{S}_I$, determined by using the method discussed in section 5.3.1. FIG. 13 shows the empirical 3D distribution of both parameters as well as the empirical distribution of each parameter. The operating range considered for each parameter is determined from the limits at 1% and 99% of each of the two distributions. The physiological range of $p_G$ values is thus comprised between $4.10^{-4}$ and $2.5.10^{-2}$ while the physiological S, values are located between $1.10^{-6}$ and $2.6.10^{-3}$. These results are also consistent with the information reported in the literature (e.g. Ronald L Prigeon, Michael E Rø der, Daniel Porte, and Steven E Kahn. The Effect of Insulin Dose on the Measurement of Insulin Sensitivity by the Minimal Model Technique Evidence for Saturable Insulin Transport in Humans. J. Clin. Invest., 97(2):501_507, 1996; R A Rizza, L J Mandarino, and J E Gerich. Dose-response characteristics for effects of insulin on production and utilization of glucose in man. American Journal of physiology. Endocrinology and metabolism, 278 (5): E794_E801, 2000 and Carmen V Doran. Modelling and control of hyperglycaemia in critical care patients. PhD thesis, University of Canterbury, Christchurch, New Zealand, 2004).

The 3D distribution of the parameters illustrated in FIG. 13 shows that the parameter values are not uniformly distributed in the plane and that a correlation exists between the $p_G$ and $S_I$ values. The distribution of the $S_I$ values for a given $P_{G_x}$ value appears to follow a normal law centred on of variable variance.

$$\overline{S}_I = 0.1 \overline{p}_G + 1.10^{-5}$$

of variable variance.

Consequently, thereafter, only the $S_I$ parameters were considered to determine the patient classes, since speaking more for the nurse, the associated $p_G$ parameters were calculated by inverting equation (5.23) for the settings. Step h of discretizing the insulin sensitivity values was chosen so as to have q=20 for the settings. The insulin sensitivity classes were established by respecting the class properties defined previously. First, the gains $\theta(S_{Ij})=(K_{pj}, T_{ij})$ were calculated for j=1 from the method presented in section 5.5.1. They are then recalculated each time that the third class property was not verified, i.e. at each creation of a new class defined by a new $S_{Ic}$ value. The results are illustrated in FIG. 14.

5.6 Application to Virtual CGAO-REA Patients
5.6.1 Virtual CGAO-REA Patients

To validate the controller settings prior to clinical trials, the actual blood glucose, insulin and glucose administration data, as well as the demographic data for the 1336 CGAO-REA patients assisted by CGAO software were used to reconstruct the stays through the glucose-insulin system pharmacodynamics model already presented in (5.1), (5.2) and (5.3). In fact, from a known trajectory of the system defined from the inputs of this system, it is possible to find the parameters so as to fit the output of the model at any point of the trajectory, or nearly so (since the model is minimalist, non-modelled or approximated physical phenomena can induce bias).

input: An $S_I$ vector of dimension q
    output: An $S_{IC}$ vector of dimension p
    initialize p;
    for j←1 to q do
    if $S_{ICp}$ is not defined or $J(S_{Ij}, \hat{\theta}(S_{ICp}))>\epsilon$ then
    // creation of a new class
    p++;
    $S_{ICp} \leftarrow S_{Ij}$;
    // calculating optimal values for class gains
    $\hat{\theta}_p(S_{ICp}) \leftarrow$ extremum_seeking $(S_{ICp}, P_{Gcp})$;
    end
    end Algorithm 1: Patient class creation algorithm Each stay is therefore associated with a parameter set $\hat{\theta}(t)=(\hat{p}_G(t), \hat{S}_I(t), \hat{\alpha}_G, \hat{\alpha}_I, \hat{k}, \hat{n}, \hat{V}_I, \hat{V}_G, \hat{F}_{end}, \hat{I}_{end}, \hat{G}_E)^T$ identified from the method presented in 5.3.1 as well as the patient demographic data (sex, height, weight, age, etc.). The estimated values of the parameters directly depend on the model inputs, i.e. information regarding glucose P(t) and insulin (u(t)) administered to the patient at a time t. Now, it has been observed that the usage conditions for the software in the CGAO-REA study control group did not enable collection of this information in a sufficiently reliable manner. In fact, since each participating centre used its own protocol (non-computerized) representing the usual practices of the centre in the control group, the collection of information in this group involved double entry of information (in their system and in the study software). In the case where, after verification, this information is not reliable enough because it was insufficiently supplied or not supplied at all, only the patients treated with CGAO were used for this analysis.

TABLE 5.3

Table of gain values according to patient insulin sensitivity

| $S_I(t_c)(10^{-3})$ | $K_P$ | $T_i$ | $T_t$ | $T_c$ |
|---|---|---|---|---|
| (2.6 ∞) | 0.01 | 3480 | 10 | 10 |
| (1.9 2.6] | 0.15 | 1400 | 10 | 10 |
| (0.9 1.9] | 0.8 | 235 | 0.4 | 0.4 |
| (0.4 0.9] | 1.6 | 115 | 0.67 | 0.67 |
| (0.3 0.4] | 1.6 | 105 | 2.0 | 2.0 |
| (0.2 0.3] | 1.7 | 102 | 5.0 | 5.0 |
| (0.0 0.2][1] | 1.7 | 102 | 5.0 | 5.0 |

Each set of parameters corresponds to a virtual CGAO-REA patient. Working with the same scenario and reinjecting the original insulin and glucose profile of the associated virtual patient, the same blood glucose must be found. The model also allows more realistically interpolating the blood glucose between measurements. Furthermore, one can also choose to apply any other insulin and glucose profile generated by another protocol or algorithm, such as CGAO_v2, for example. FIG. 15 shows the result of the control of two different algorithms applied to a virtual CGAO-REA patient. In the first case, a PID controller with gain sequencing similar to the one studied in this section was applied. For comparison, the algorithm used in the NICE-SUGAR study (Simon Finfer, Dean R Chittock, Steve YuShuo Su, Deborah Blair, Denise Foster, Vinay Dhingra, Rinaldo Bellomo, Deborah Cook, Peter Dodek, William R Henderson, Paul C HObert, Stephane Heritier, Daren K Heyland, Colin Mcarthur, Ellen Mcdonald, Imogen Mitchell, John A Myburgh, Robyn Norton, Julie Potter, Bruce G Robinson, and Juan J Ronco. Intensive versus Conventional Glucose Control in Critically Ill Patients. The New England journal of medicine, 360(13): 1283_1297, 2009 and Simon Finfer. https://studies.thegeorgeinstitute.org/nice/, 2009)

5.6.2 Results of the Simulations

In a second step, the settings were tested by simulation in virtual patients previously created who had a stay duration longer than two days. Of the 1336 virtual patients available, 1268 fulfilled this criterion. For these in silico tests, metrics such as mean blood glucose, time spent within the targets [4.4, 6.1] and [4.4, 10.0], the percentage of patients who had exhibited at least one severe hypoglycaemic episode and the mean and standard deviation of the intervals between measurements were calculated over the first 7 days only.

The results are shown in Table 5.4. For these tests, no measurement noise induced by the use of glucometers or even delays due to nurse workload were considered.

TABLE 5.4

Performance of the CGAO_v2 controller set with the extremum search setting method then applied to 1268 virtual patients.

| Description | Mean | Median | Interquartiles |
|---|---|---|---|
| Mean blood glucose (mmol/L) | 6.0 | 5.8 | [5.5-6.3] |
| Time elapsed between [4.4, 6.1] mM (%) | 47.8 | 48.2 | [39.1-57.6] |
| Time elapsed between [4.4, 10.0] mM (%) | 83.6 | 85.9 | [78.7-91.2] |
| Severe hypoglycaemia (%) | 19.5 | — | |
| Mean time interval per patient (min) | 110 | 110 | [98-123] |
| Mean standard deviation between time intervals per patient (min) | 50 | 51 | [47-55] |

TABLE 5.5

Table of gain values according to patient insulin sensitivity then applied to 1268 virtual patients.

| $S_I(t_c)(10^{-3})$ | $K_P$ | $T_i$ | $T_t$ | $T_c$ |
|---|---|---|---|---|
| (2.6 ∞) | 0.5 | 1600 | 3200 | 3200 |
| (1.9 2.6] | 0.8 | 800 | 1600 | 1600 |
| (0.9 1.9] | 0.9 | 770 | 940 | 940 |
| (0.4 0.9] | 1.0 | 705 | 470 | 470 |
| (0.3 0.4] | 1.1 | 675 | 470 | 470 |
| (0.2 0.3] | 1.2 | 675 | 470 | 470 |
| (0.0 0.2]² | 1.2 | 675 | 470 | 470 |

During these 1268 stays, more than 120,000 virtual blood glucose measurements were done, with a mean in the upper part of the target. The time elapsed within target is around 50% with between-measurement intervals of around two hours, a duration in agreement with the times observed in reality during the study. The percentage of severe hypoglycaemia episodes is very high (19.5%). It is probable that the significant decrease of blood glucose level leads to an increase in severe hypoglycaemia rates, given that the standard deviations of the two blood glucose distributions of the real cohort and the virtual cohort are not significantly different (2.02 mM and 2.12 mM, respectively).

In view of clinical trials, the gains were touched up on a case by case basis to approach the nursing strategy of expert centres (number of inclusions >200). Several patients representative of each class and whose blood glucose control was deemed satisfactory, in terms of time spent within the target, were then identified. The gains were regulated so as to minimize the squared difference between the flow rates actually applied by the nurse(s) and the flow rate recommendations of the controller, rather than considering the distance to the target as optimization criterion.

These simulations were repeated with these new settings. The results are shown in Table 5.6. The mean standard deviation in this case is 1.92 mM. It is therefore lower than with the previous settings, although these performances do not reach the target and the time spent within the target is significantly lower than previously. The rate of severe hypoglycaemic episodes consequently decreased by half (10.2% vs. 19.5% with the previous settings). The recommended and applied time interval was not changed.

TABLE 5.6

Performance of the CGAO_v2 controller set on the nursing strategy.

| Description | Mean | Median | Interquartiles |
|---|---|---|---|
| Mean blood glucose (mmol/L) | 6.6 | 6.4 | [6.0-7.1] |
| Time elapsed between [4.4, 6.1] mM (%) | 37.6 | 36.5 | [25.6-47.7] |
| Time elapsed between [4.4, 10.0] mM (%) | 88 | 91.3 | [83.4-95.9] |
| Severe hypoglycaemia (%) | 10.2 | — | — |
| Mean time interval per patient (min) | 118 | 118 | [105-132] |
| Mean standard deviation between time intervals per patient (min) | 46 | 46 | [42-51] |

5.7 Conclusion

The term "performance" is a well-defined concept in automation. An effective PI controller in automation is a controller that can reach the objective set for it with precision (i.e., the measured output is slaved to the desired output) in a very short time, while maintaining good stability (i.e. preventing "over/undershoots" or oscillations around the target). This is reflected by:

$$\int_{t_0}^{t_F} |e(\tau)| d\tau < \varepsilon \quad (5.24)$$

where $e(t)=G(t)-G_{ref}$ and $t_0$ and $t_F$ the start and end time for the stay in our case, respectively. However, this definition of performance where one seeks to prevent any oscillation and to rally the target in a very short time is not in agreement with the concept of glycaemic range used by doctors. In addition, studies have shown that a high and rapid variation in blood glucose was detrimental to cells, or that repeated hypoglycaemic episodes had an impact on patient mortality. However, there are oscillations called ultradian, slow and natural oscillations that are observed in healthy individuals when glucose levels are in the normal range (James Keener and James Sneyd. Mathematical Physiology II—Systems Physiology. Keener2008, 2008) and whose period is about 120 min. Naturally, the first question to ask is "How do we define a glycaemic controller as being effective at its task?" This begins by defining the metrics of central tendency of blood glucose, glycaemic variability or minimum blood glucose all related to mortality, as shown by Mackenzie et al. in 2011 (lain M J Mackenzie, Tony Whitehouse, and Peter G Nightingale. The metrics of glycaemic control in critical care. Intensive care medicine, 37(3): 435-43, March 2011).

The invention claimed is:

1. A method for controlling the administration of insulin to a patient, comprising:
    setting a target glucose level,
    computing, using a controller, a recommended infusion rate for administering insulin to the patient based on the target glucose level and a measured glucose level of the patient determined using a sensor device, wherein the controller uses a controller gain for computing the recommended infusion rate,
    determining an insulin sensitivity of the patient using a mathematical model based on the measured glucose level and an actual infusion rate of insulin administered to the patient,
    determining, based on the insulin sensitivity, the controller gain of the controller, wherein the controller gain for computing the recommended infusion rate is determined by associating the insulin sensitivity to one of a plurality of predefined insulin sensitivity classes, each insulin sensitivity class having boundaries defined by measures of stability and robustness related to controller behavior and being associated with a predefined controller gain such that by associating the insulin sensitivity to an insulin sensitivity class, the controller gain is determined to be the controller gain of the associated insulin sensitivity class, wherein each insulin sensitivity class is defined by associated ranges of a stability parameter and a robustness parameter determined based on the insulin sensitivity, and
    administering insulin at the recommended infusion rate to the patient using an infusion pump.

2. The method according to claim 1, wherein the controller computes the recommended infusion rate based on the target glucose level and the measured glucose level and in addition based on a glucose intake value of the patient.

3. The method according to claim 1, wherein the controller computes a proposed time for next measurement for measuring a glucose level of a patient.

4. The method according to claim 1, wherein the model is used to determine the insulin sensitivity of the patient anew for each measured glucose level, wherein the controller gain is set anew based on the insulin sensitivity of the patient determined anew for each measured glucose level and the controller computes the recommended infusion rate based on a current measured glucose level and a target glucose level using the controller gain set anew based on the insulin sensitivity of the patient determined anew for each measured glucose level.

5. The method according to claim 1, wherein the model is a PkPd model taking into account patient-specific parameters, the measured glucose level, the actual infusion rate and a glucose intake value and estimating the insulin sensitivity.

6. The method according to claim 1, wherein, if it is determined that for a time of measurement the insulin sensitivity is associated with a different insulin sensitivity class than for a previous time of measurement, the controller gain is set according to the insulin sensitivity class determined for the time of measurement only if a predefined additional switch criterion is satisfied.

7. The method according to claim 1, wherein multiple insulin sensitivity classes are determined prior to administering insulin to the patient.

8. The method according to claim 1, wherein the controller outputs the recommended infusion rate and awaits approval or modification of the recommended infusion rate by a nurse prior to administering insulin to the patient.

9. The method according to claim 1, wherein the controller is a PID controller.

10. The method according to claim 1, wherein the controller is defined by a PID controller equation having a proportional term, an integral term and a derivative term and further comprising a compliance term for taking into account, when determining a new recommended infusion rate, a deviation of the actual infusion rate from a previously determined recommended infusion rate.

11. The method according to claim 10, wherein the controller uses, as controller gain, a set of gains associated with the proportional term, the integral term and the derivative term of the PID controller equation.

12. The method according to claim 1, wherein the controller uses a saturation mechanism according to which the recommended infusion rate is limited to a range of allowable infusion rates.

13. The method according to claim 1, wherein determining the insulin sensitivity of the patient using a mathematical model occurs in real time, and associating the insulin sensitivity to a predefined insulin sensitivity class occurs in real time.

14. A control device for controlling the administration of insulin to a patient, comprising:

a target setting unit for setting a target glucose level, a controller for computing a recommended infusion rate for administering insulin to the patient based on the target glucose level and a measured glucose level of the patient using a sensor device, wherein the controller uses a controller gain for computing the recommended infusion rate, a model unit configured to determine an insulin sensitivity of the patient with a mathematical model based on the measured glucose level and an actual infusion rate of insulin administered to the patient and an adaption unit for determining based on the insulin sensitivity, the controller gain of the controller, wherein the adaption unit is configured to determine the controller gain for computing the recommended infusion rate by associating the insulin sensitivity to one of a plurality of predefined insulin sensitivity classes, each insulin sensitivity class having boundaries defined by measures of stability and robustness related to controller behavior and being associated with a predefined controller gain such that by associating the insulin sensitivity to an insulin sensitivity class, the controller gain is determined to be the controller gain of the associated insulin sensitivity class, wherein each insulin sensitivity class is defined by associated ranges of a stability parameter and a robustness parameter determined based on the insulin sensitivity; and an output connectable to an infusion pump for administering insulin at the recommended infusion rate to the patient to feed the infusion pump the recommended infusion rate.

15. The control device according to claim 14, wherein the mathematical model is a PkPd model.

16. The control device according to claim 14, wherein the model unit is configured to determine the insulin sensitivity of the patient with a mathematical model in real time, and the adaption unit associates the insulin sensitivity to a predefined insulin sensitivity class in real time.

* * * * *